(12) United States Patent
Rapraeger

(10) Patent No.: US 9,505,818 B2
(45) Date of Patent: Nov. 29, 2016

(54) SYNDECAN PEPTIDES AND POLYPEPTIDES AS INHIBITORS OF CANCER

(71) Applicant: Wisconsin Alumni Research Foundation, Madison, WI (US)

(72) Inventor: Alan Rapraeger, Stoughton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/688,927

(22) Filed: Apr. 16, 2015

(65) Prior Publication Data

US 2015/0218241 A1  Aug. 6, 2015

Related U.S. Application Data

(62) Division of application No. 13/936,854, filed on Jul. 8, 2013, now Pat. No. 9,034,827.

(60) Provisional application No. 61/782,588, filed on Mar. 14, 2013, provisional application No. 61/669,544, filed on Jul. 9, 2012.

(51) Int. Cl.
*A61K 38/00* (2006.01)
*C07K 14/47* (2006.01)
*C07K 14/705* (2006.01)

(52) U.S. Cl.
CPC ..... *C07K 14/4703* (2013.01); *C07K 14/70596* (2013.01); *C07K 2319/23* (2013.01)

(58) Field of Classification Search
None
See application file for complete search history.

(56) References Cited

U.S. PATENT DOCUMENTS

| | | |
|---|---|---|
| 2008/0020979 A1 | 1/2008 | Rapraeger |
| 2013/0252895 A1 | 9/2013 | Rapraeger |

OTHER PUBLICATIONS

Liu et al Dev. Growth Differ. 46:37-51 (2004).*
Amano et al., "Bone morphogenetic protein 1 is an extracellular processing enzyme of the laminin 5 gamma 2 chain", *J. Biol. Chem.*, 275(30):22728-22735, 2000.
Carulli et al., "Cell surface proteoglycans syndecan-1 and -4 bind overlapping but distinct sites in laminin α3 LG45 protein domain", *J. Biol. Chem.*, 287(15):12204-12216, 2012.
Dermer, "Another anniversary for the war on cancer," *Bio/Technology*, 12:320, 1994.
Freshney, "Culture of Animal Cells, a Manual of Basic Technique," p. 4, 1983.
Goldfinger et al., "Processing of laminin-5 and its functional consequences: role of plasmin and tissue-type plasminogen activator", *J. Cell Biol.*, 141(1):255-265, 1998.
Goldfinger et al., "The alpha3 laminin subunit, alpha6beta4 and alpha3beta1 integrin coordinately regulate wound healing in cultured epithelial cells and in the skin", *J. Cell Sci.*, 112(Pt 16):2615-2629, 1999.
Gura, "Systems for identifying new drugs are often faulty," *Science*, 278:1041-1042, 1997.
Jain, "Barriers to drug delivery in solid tumors," *Sci. Am.*, 271:58-65, 1994.
Marinkovich et al., "The anchoring filament protein kalinin is synthesized and secreted as a high molecular weight precursor", *J. Biol. Chem.*, 267(25):17900-17906, 1992.
Matsui et al., "The assembly of laminin-5 subunits", *J. Biol. Chem.*, 270:23496-23503, 1995.
Maxmen, "In This Issue", *JEM*, 206(3):492-493, 2009.
Office Action issued in U.S. Appl. No. 13/936,854, mailed Jul. 15, 2014.
Office Action issued in U.S. Appl. No. 13/936,854, mailed May 2, 2014.
Tran et al., "Targeting a tumor-specific laminin domain critical for human carcinogenesis", *Cancer Res.*, 68(8):2885-2894, 2008.
Wang et al., "Interaction of syndecan and alpha6beta4 integrin cytoplasmic domains: regulation of ErbB2-mediated integrin activation", *J. Biol. Chem.*, 285:13569-13579, 2010.

* cited by examiner

*Primary Examiner* — Sheela J Huff
(74) *Attorney, Agent, or Firm* — Boyle Fredrickson, S.C.

(57) ABSTRACT

The invention provides for peptides from syndecan 1 and methods of use therefor. These peptides can inhibit α4β6 interaction with HER2, thereby preventing tumor cell growth and tissue invasion.

21 Claims, 13 Drawing Sheets

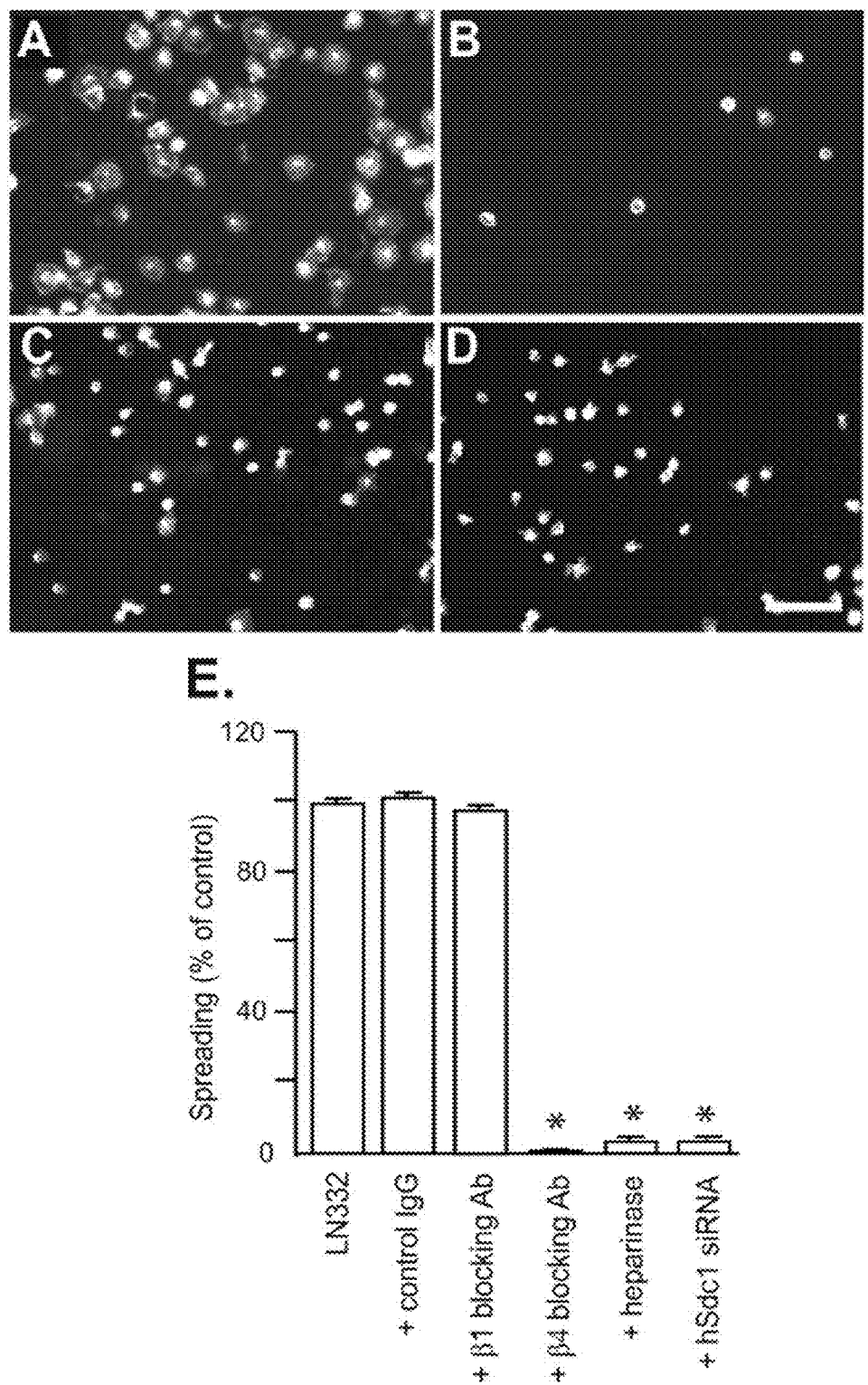
FIG. 2A-E

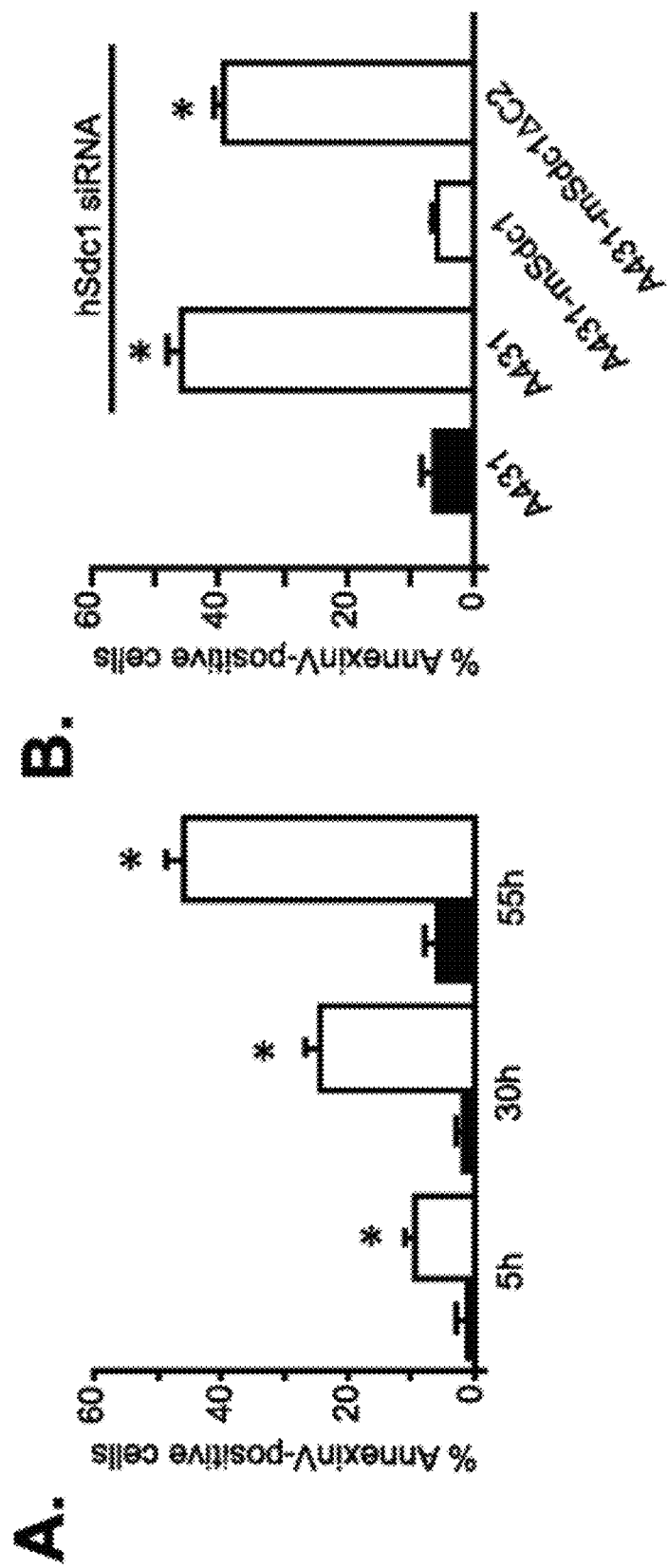
FIG. 3A-B

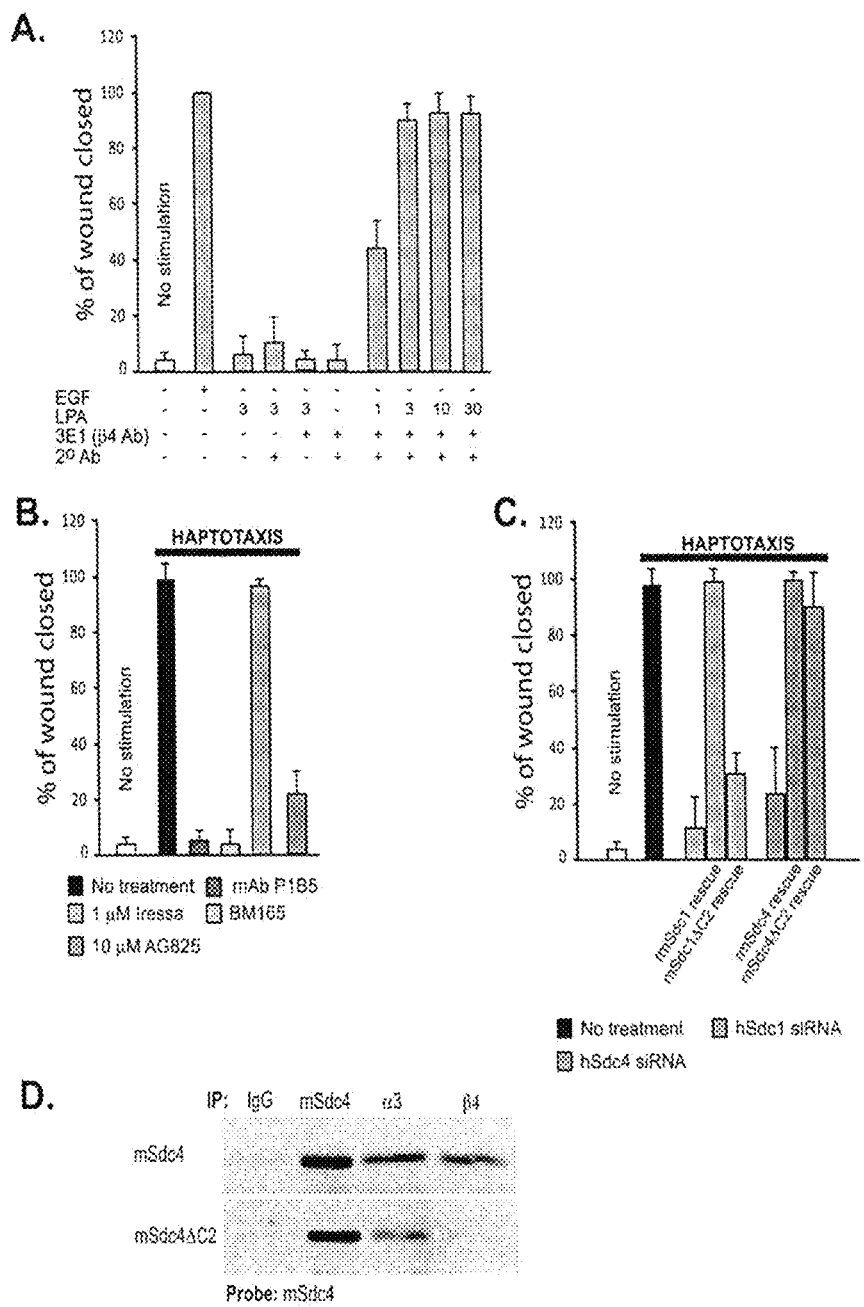
FIG. 6A-D

A.

```
          C1                  V              C2
Sdc1  RMKKKDEGSYSLEEPKQANGGAYQKPTKQEEFYA³⁰¹

Sdc4  RMKKKDEGSYDLG-KKP---IYKKAPTN--EFYA¹⁹⁸
```

B.

$$A^{1729} \quad A^{1733}$$

β4 ....TRHVTQEFVSRTLTTSGTLSTHMDQQFFQT$^{1752}$ truncate
Δ1729-1752

FIG. 7A-B

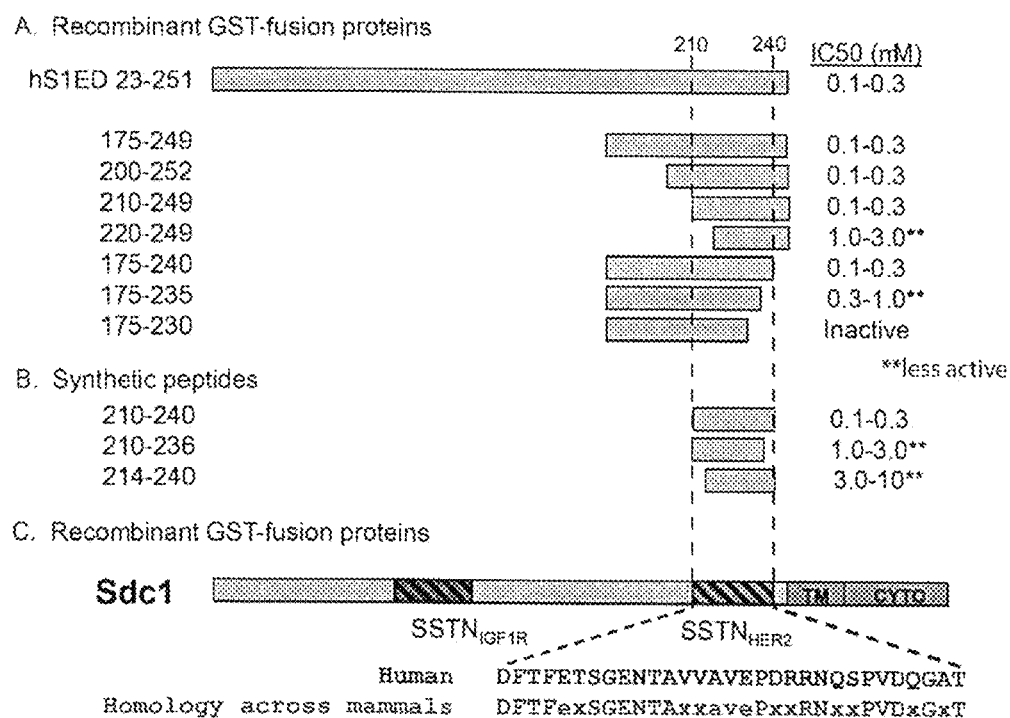
FIG. 10A-C

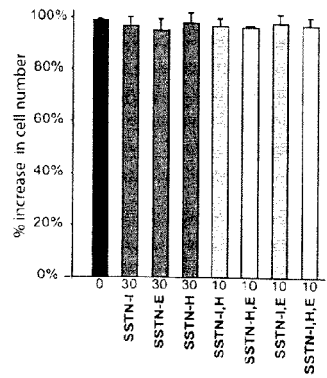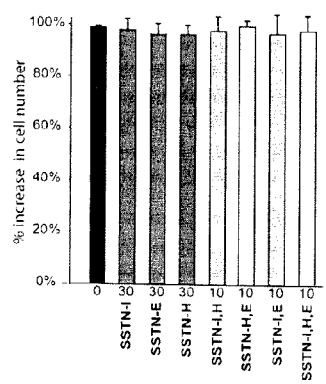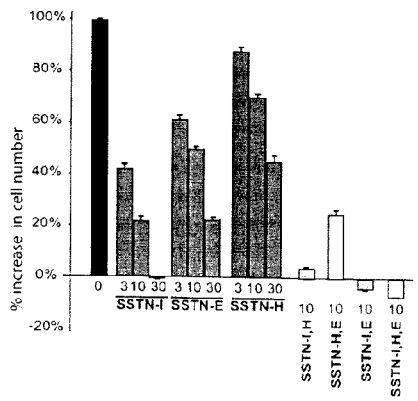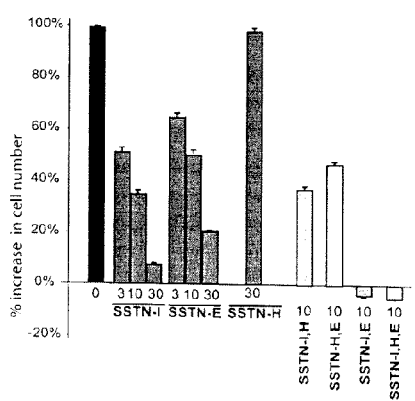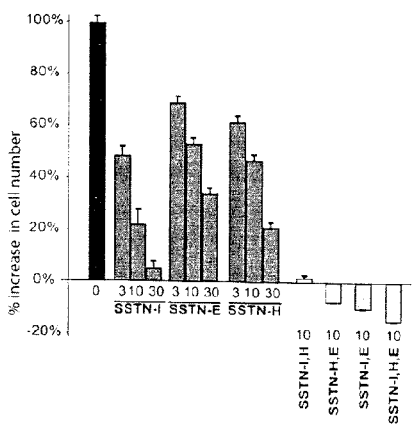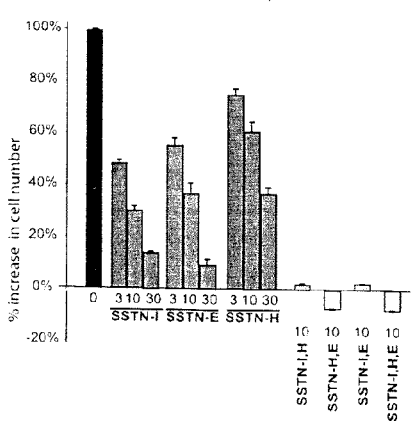
FIG. 11A-F

SYNDECAN PEPTIDES AND POLYPEPTIDES AS INHIBITORS OF CANCER

PRIORITY CLAIM

The present application is a divisional of U.S. application Ser. No. 13/936,854, filed Jul. 8, 2013, which claims benefit of priority to U.S. Provisional Application No. 61/669,544, filed Jul. 9, 2012, and U.S. Provisional Application No. 61/782,588, filed Mar. 14, 2013, the entire contents of each application being hereby incorporated by reference.

FEDERAL FUNDING CLAUSE

This invention was made with government support under CA109010 and CA139872 awarded by the National Institutes of Health. The government has certain rights in the invention.

SEQUENCE LISTING

Pursuant to 37 C.F.R. 1.821(c), a sequence listing is submitted herewith as an ASCII compliant text file named "WARFP0044USD1.txt" created on Apr. 2, 2015 and having a size of ~12 KB. The content of the aforementioned file is hereby incorporated by reference in its entirety.

BACKGROUND OF THE INVENTION

1. Field of the Invention

This invention relates to regulation of cell growth, and more particularly to regulation of cancer cell growth. In particular, peptides and polypeptides derived from particular regions of the syndecan 1 have been shown to inhibit engagement of α6β4 integrin by HER2, thereby limiting tissue invasion and tumor cell survival.

2. Related Art

EGFR family receptor tyrosine kinases are causal factors in cancer, especially in breast cancer. HER2 is overexpressed, typically via gene amplification, in 25-30% of breast tumors (HER2+ breast cancer), leading to poor overall survival (Berger et al., 1988; Slamon et al., 1987). Expression of the α6β4 integrin is also upregulated in cancer, often along with the expression of receptor tyrosine kinases such as HER2 that link with the integrin and activate it to drive tumor cell proliferation, survival and invasion. Identified as the TSP-180 antigen in mouse tumors (Falcioni et al., 1986), or the A9 antigen in humans (Van Waes et al., 1991; Kimmel and Carey, 1986), high expression of this antigen predicts a higher rate of early relapse in head and neck squamous cell carcinoma (Wolf et al., 1990; Carey et al., 1987). In more recent studies exploring its tumor-promoting role using animal models, keratinocytes that lack expression of the β4 integrin subunit fail to form invasive squamous cell carcinomas when transformed with ras and IκB, unlike their normal counterparts that express the integrin (Dajee et al., 2003; Tran et al., 2008). Despite this seeming importance of the integrin in squamous cell carcinoma, there currently are no therapeutics available to target its tumor-promoting activities. The α6β4 integrin is also expressed on vascular endothelial cells in vivo, where its function in hemidesmosomes allows the endothelium to resist frictional forces as it does on stratified epithelia. Giancotti has shown a clear role for α6β4 integrin in tumor angiogenesis and that α6β4 is expressed in the vasculature of several tumor types (prostate, breast, glioma, papillary thyroid, melanoma) (Nikolopoulos et al., 2004). Although not studied extensively, it clear that endothelial cells express EGFR family members, including the HER2 kinase (Amin et al., 2006).

It is increasingly appreciated that growth factor receptors and extracellular matrix receptors work closely together to regulate cell proliferation, invasion and survival, and may do so as macromolecular assemblies at the cell surface. Indeed, HER2 is known to be coupled with the α6β4 integrin and signaling from this receptor assembly is implicated in both tumorigenesis and tumor-induced angiogenesis. However, the means by which these receptors are coupled remains largely unknown. Work from a variety of laboratories has shown a linkage between the α6β4 integrin and HER2 in breast and other cancers (Folgiero et al., 2008; Lu et al., 2008). This integrin in normal cells assembles with laminin in the basement membrane underlying basal epithelial cells as well as endothelial cells lining blood vessels, forming stable hemidesmosomes in which the long (ca. 1000 amino acid) cytoplasmic domain of the β4 subunit anchors to the keratin filament network in the cytoplasm of the cell (Hopkinson and Jones, 2000; Nievers et al., 1999; Wilhelmsen et al., 2006). In contrast to this "stabilizing" role, however, the integrin takes part in the invasion, proliferation and survival of tumors that overexpress the receptor tyrosine kinases HER2, EGFR, or c-Met—leading to the assembly of these kinases with the integrin (Wilhelmsen et al., 2006; Agazie and Hayman, 2003; Mainiero et al., 1996; Mariotti et al., 2001; Bertotti et al., 2005; Bertotti et al., 2006; Bon et al., 2007; Falcioni et al., 1997; Gambaletta et al., 2000; Santoro et al., 2003; Trusolino et al., 2001; Tsuruta et al., 2008; Giancotti, 2007). When coupled with the integrin, signaling from these kinases disrupts the hemidesmosome (Rabinovitz et al., 2004; Wilhelmsen et al., 2007) and leads to tyrosine phosphorylation of the β4 cytoplasmic domain, providing docking sites for signaling effectors that drive tumor cell proliferation, invasion and survival (Wilhelmsen et al., 2006; Mariotti et al., 2001; Bertotti et al., 2006; Wilhelmsen et al., 2007; Mainiero et al., 1997; Shaw et al., 1997; Guo et al., 2006; Merdek et al., 2007; Dutta and Shaw, 2008; Datta et al., 1999; Dans et al., 2001; Shaw et al., 2001; Yang et al., 2010). The distal third of the β4 tail containing these phosphorylation sites has thus been termed the β4 "signaling domain" (Guo et al., 2006) (FIG. 1). In studies using the MMTV-Neu mouse model of HER2+ breast cancer, replacement of native β4 with a β4 mutant ($β4^{1355T}$) lacking this signaling domain acts as a suppressor of breast cancer (Guo et al., 2006), suggesting that the wild type β4 receptor normally couples with HER2 to drive tumorigenesis in human HER2+ breast cancer as well. Work utilizing a number of mammary carcinoma cell lines, focusing mostly on HER2+ cells, also shows that HER2/α6β4 signaling is critical for invasion and survival of these tumors (Falcioni et al., 1997; Gambaletta et al., 2000; Guo et al., 2006). Complementing their expression in the tumors, HER2 and EGFR are also expressed in endothelial cells, especially those induced by tumors (Amin et al., 2006; Bruns et al., 2000; Kedar et al., 2002), and couple with the α6β4 integrin during tumor-induced angiogenesis (Nikolopoulos et al., 2004). What remains unanswered is how the receptor tyrosine kinase associates with the integrin to initiate this process. The answer to this question could reveal significant therapeutic opportunities in the treatment of cancer.

SUMMARY OF THE INVENTION

Thus, in accordance with the present invention, there is provided an isolated and purified peptide segment consisting of between 30 and 100 amino acid residues and comprising residues 210-235 of SEQ ID NO:1. The peptide may be 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length. The peptide may be between 31 and 80 amino acid residues in length. The peptide may be between 31 and 61 amino acid residues in length. The peptide may be between 61 and 80 amino acid residues in length. The peptide may be between 66 and 80 amino acid residues in length. The peptide may consist essentially of residues 210-235 (SEQ ID NO: 2) or residues 210-240 (SEQ ID NO 3). The peptide may comprise residues 210-240 (SEQ ID NO: 3). The peptide may consist essentially of residues 210-240 (SEQ ID NO: 3), 210-249 (SEQ ID NO: 4), 175-235 (SEQ ID NO: 5) or 175-240 (SEQ ID NO: 6). The peptide may consist of residues 210-240 (SEQ ID NO: 3), 210-249 (SEQ ID NO: 4), 175-235 (SEQ ID NO: 5) or 175-240 (SEQ ID NO: 6). The peptide may be between 40 and 61 amino acid residues in length.

In another embodiment, there is provided a nucleic acid encoding a peptide segment consisting of between 30 and 100 amino acid residues and comprising residues 210-235 of SEQ ID NO:1. The nucleic acid may encode a peptide of 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length. The nucleic acid may encode a peptide of between 31 and 80 amino acid residues in length. The peptide may be between 31 and 61 amino acid residues in length. The nucleic acid may encode a peptide of between 61 and 80 amino acid residues in length. The nucleic acid may encode a peptide of between 66 and 80 amino acid residues in length. The nucleic acid may encode a peptide consisting essentially of residues 210-235 (SEQ ID NO: 2) or residues 210-240 (SEQ ID NO 3). The nucleic acid may encode a peptide comprising residues 210-240 (SEQ ID NO: 3). The nucleic acid may encode a peptide consisting essentially of residues 210-240 (SEQ ID NO: 3), 210-249 (SEQ ID NO: 4), 175-235 (SEQ ID NO: 5) or 175-240 (SEQ ID NO: 6). The nucleic acid may encode a peptide consisting of residues 210-240 (SEQ ID NO: 3), 210-249 (SEQ ID NO: 4), 175-235 (SEQ ID NO: 5) or 175-240 (SEQ ID NO: 6). The nucleic acid may encode a peptide of between 40 and 61 amino acid residues in length.

In yet another embodiment, there is provided a method of inhibiting $\alpha 6\beta_4$ integrin interaction with HER2/Neu comprising contacting a HER2/Neu molecule with a peptide segment consisting of between 30 and 100 amino acid residues and comprising 210-235 of SEQ ID NO:1. The peptide or polypeptide may be 31, 35, 40, 45, 49, 50, 55, 60, 65, 70, 75, 80, 85, 90, 95 or 100 amino acid residues in length, or between 31 and 80 amino acid residues in length, or between 31 and 61 amino acid residues in length, or between 61 and 80 amino acid residues in length or between 66 and 80 amino acid residues in length. The peptide may consist essentially of residues 210-235 (SEQ ID NO: 2) or residues 210-240 (SEQ ID NO 3). The peptide may comprise residues 210-240 (SEQ ID NO: 3). The peptide may consist essentially of residues 210-249 (SEQ ID NO: 4), 175-235 (SEQ ID NO: 5) or 175-240 (SEQ ID NO: 6). The peptide may consist of residues 210-240 (SEQ ID NO: 3), 210-249 (SEQ ID NO: 4), 175-235 (SEQ ID NO: 5) or 175-240 (SEQ ID NO: 6). The $\alpha 6\beta_4$ integrin is located on the surface of a cell. The cell may be a cancer cell, such as a carcinoma, a myeloma, a melanoma, a schwannoma, a malignant peripheral nerve sheath tumor cell, a malignant endothelial cell or a glioma. The method may further comprise contacting said cancer cell with a second cancer inhibitory agent. The cancer cell may be a metastatic cancer cell or tumor stem cell. The step of contacting may comprise providing to said cell an expression construct comprising a nucleic acid encoding a peptide segment consisting of between 31 and 100 amino acid residues and comprising residues 210-240 of SEQ ID NO:1 operably linked to a promoter active in said cell.

In still yet a further embodiment, there is provided a method of screening for an agent that inhibits the binding of syndecan-1 and HER2/Neu comprising (a) providing a syndecan-1 or a fragment thereof and a HER2/Neu or a fragment thereof, wherein said syndecan-1 or a fragment thereof and a HER2/Neu or a fragment thereof are capable of binding each other; (b) contacting the proteins or fragments of step (a) with a candidate substance; and (c) assessing the binding of said syndecan-1 or a fragment thereof and said HER2/Neu or a fragment thereof, wherein reduced binding in step (c) as compared to the binding in the absence of said candidate substance identifies said candidate substance as an agent that inhibits the binding of syndecan-1 and HER2/Neu. The candidate substance maybe a protein, a peptide, a peptidometic, a polynucleotide, an oligonucleotide, or a small molecule. One or both of said syndecan-1 or a fragment thereof and said HER2/Neu or a fragment thereof may be labeled with a detectable label. Step (c) may comprise FRET, immunodetection, a gel-shift assay, or a phosphorylation assay. The candidate substance may be a peptide segment consisting of between 31 and 100 amino acid residues and comprising residues 210-240 of SEQ ID NO: 1. Step (a) may further comprise including $\alpha 6\beta_4$ or a fragment thereof that interacts with syndecan-1 and/or HER2/Neu. The method may further comprise a control reaction of assessing the binding of said syndecan-1 or a fragment thereof and said HER2/Neu or a fragment thereof in the absence of said candidate substance. Steps (a)-(c) may be performed in a cell-free system, performed in a cell or performed in vivo.

In a further embodiment, there is provided a method of treating a subject with a cancer, cancer cells of which express $\alpha 6\beta_4$ integrin and HER2/Neu, comprising contacting said cells with a peptide segment consisting of between 30 and 100 amino acid residues and comprising residues 210-235 of SEQ ID NO: 1. The peptide may be 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length, or between 31 and 80 amino acid residues in length, or between 31 and 61 amino acid residues in length, or between 61 and 80 amino acid residues in length, or between 66 and 80 amino acid residues in length. The peptide may consist essentially of residues 210-235 (SEQ ID NO: 2) or residues 210-240 (SEQ ID NO: 3). The peptide may comprise residues 210-240 (SEQ ID NO: 3). The peptide may consist essentially of residues 210-240 (SEQ ID NO: 3), 210-249 (SEQ ID NO: 4), 175-235 (SEQ ID NO: 5) or 175-240 (SEQ ID NO: 6). The peptide may consist of residues 210-240 (SEQ ID NO: 3), 210-249 (SEQ ID NO: 4), 175-235 (SEQ ID NO: 5) or 175-240 (SEQ ID NO: 6). The subject may be a human or a non-human mammal. The cancer may be a carcinoma, a myeloma, a melanoma or a glioma. The peptide may be administered directly to said cancer cells, local to said cancer cells, regional to said cancer cells, or systemically. The method may further comprise administering to said subject a second cancer therapy selected from chemotherapy, radiotherapy, immunotherapy, hormonal therapy, or gene therapy. The method may further comprise administering said peptide to said subject more than once.

In yet a further embodiment, there is provided a method of inhibiting scarring in a subject to comprising administering to said subject a peptide segment consisting of between 30 and 100 amino acid residues and comprising residues 210-235 of SEQ ID NO: 1. The peptide or polypeptide may be 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length, or between 31 and 80 amino acid residues in length, or between 31 and 61 residues in length, or between 61 and 80 amino acid residues in length, or between 66 and 80 amino acid residues in length. The peptide may consist essentially of residues 210-235 (SEQ ID NO: 2) or residues 210-240 (SEQ ID NO: 3). The peptide may comprise residues 210-240 (SEQ ID NO: 3). The peptide may consist essentially of residues 210-240 (SEQ ID NO: 3), 210-249 (SEQ ID NO: 4), 175-235 (SEQ ID NO: 5) or 175-240 (SEQ ID NO: 6). The peptide may consist of residues 210-240 (SEQ ID NO: 3), 210-249 (SEQ ID NO: 4), 175-235 (SEQ ID NO: 5) or 175-240 (SEQ ID NO: 6). The peptide may be between 40 and 61 amino acid residues in length.

In still yet a further embodiment, there is provided a method of inhibiting pathologic neovascularization comprising administering to said subject a peptide segment consisting of between 30 and 100 amino acid residues and comprising residues 210-235 of SEQ ID NO: 1. The peptide or polypeptide may be 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length, or between 31 and 80 amino acid residues in length, or between 31 and 61 amino acid residues in length, or between 61 and 80 amino acid residues in length, or 66 and 80 amino acid residues in length. The peptide may consist essentially of residues 210-235 (SEQ ID NO: 2) or residues 210-240 (SEQ ID NO: 3). The peptide may comprise residues 210-240 (SEQ ID NO: 3). The peptide may consist essentially of residues 210-240 (SEQ ID NO: 3), 210-249 (SEQ ID NO: 4), 175-235 (SEQ ID NO: 5) or 175-240 (SEQ ID NO: 6). The peptide may consist of residues 210-240 (SEQ ID NO: 3), 210-249 (SEQ ID NO: 4), 175-235 (SEQ ID NO: 5) or 175-240 (SEQ ID NO: 6). The peptide may be between 40 and 61 amino acid residues in length. The pathological neovascularization may involve activated vascular endothelial cells.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIGS. 2A-E. Requirement of syndecan-1 for A431 cell spreading on LN332. A431 cervical carcinoma cells plated on slides coated with 10 µg/ml LN332 (FIG. 2A) without treatment; (FIG. 2B) with blocking antibody 3E1 to $\alpha6\beta4$; (FIG. 2C) prior treatment with heparinase III; or (FIG. 2D) prior treatment with siRNA specific for human Sdc1. (FIG. 2E) Quantification of spread cells plated on LN332 and treated with blocking antibody to $\beta1$ integrin (mAb13 30 µg/ml) or control IgG (20 µg/ml), 3E1 blocking antibody (20 ug/ml) to $\beta4$ integrin, heparinase III (0.4 CU/ml) or human Sdc1 siRNA (100 nM). Data represent triplicate experiments+/−S.D. (Wang et al., 2010).

FIGS. 3A-D. Sdc1-dependent signaling by $\alpha6\beta4$ prevents apoptosis in A431 cells. (FIG. 3A) A431 cells were grown in serum-containing medium for 5, 30 and 55 h following pre-treatment with lipofectamine with or without hSdc1-specific siRNA. The number of apoptotic cells was determined by staining with Annexin V and expressed as a percentage of the total cells. (FIG. 3B) A431 cells expressing either empty vector or vector encoding mSdc1 or mSdc1ΔC2 mutant were treated with or without siRNA, then plated for 55 hr in serum-containing medium followed by staining with Annexin V. (FIG. 3C) A431 cells were pretreated with lipofectamine alone or lipofectamine with hSdc1-specific siRNA, then were plated in serum-containing medium for 30 hr in 20 µg/ml mAb 3E1 to block ligand binding to the $\alpha6\beta4$ integrin, or treated with mAb 3E1 plus anti-mouse IgG to cluster the $\alpha6\beta4$ integrin to rescue the block to integrin signaling. Cells were suspended and stained with Annexin V. (FIG. 3D) Quantification of apoptosis monitored by Annexin V staining under the conditions defined in (FIG. 3C). Data are from triplicate experiments+/−S.D. (Wang et al., 2010).

FIG. 6A-D. Sdc1 is required for HER2/α6β4-dependent HaCat keratinocyte migration. (FIG. 6A) HaCat keratinocytes deposit laminin 332 (LN332) and migrate upon this using α3β1 and α6β4 integrins to close a scratch wound in the monolayer when stimulated to undergo chemotaxis in response to EGF. Alternatively, migration is induced by clustering the integrin (using mAb 3E1 against the integrin+a secondary antibody to cluster the first antibody and thus the entire complex) in the presence of LPA. This mimics the clustering that occurs when the cells engage LN332 and is referred to as haptotaxis. Note that cells do not migrate in response to LPA alone. (FIG. 6B) Haptotaxis, stimulated by LPA and clustering of α6β4 integrin as described in FIG. 6A, is blocked by antibody directed against the α3β1 integrin or by BM165 which targets the binding site for α3β1 in LN332. Note that haptotaxis depends on HER2, as it is blocked by 10 μM tyrphostin AG825 that blocks HER2, and not by 1 μM Iressa, which blocks EGFR. (FIG. 6C) The potential roles of Sdc1 or Sdc4 in haptotaxis is tested by silencing their expression, together with attempting to rescue with either wild-type mouse Sdc1 or Sdc4, or mouse mutants unable to engage the β4 cytoplasmic domain (mSdc1 C2 or mSdc4 C2). Haptotaxis is blocked by silencing endogenous Sdc1, and this cannot be rescued by Sdc1ΔC2 that fails to engage the α6β4 integrin. Silencing Sdc4 also disrupts migration, but this traces to its role in activity of the α3β1 integrin and not a role in engaging the α6β4 integrin, as it can be rescued by mSdc4ΔC2 that fails to associate with the α6β4 integrin. (FIG. 6D) Immunoprecipitation of either native mSdc4 or mSdc4 C2 confirms that the mSdc4ΔC2 mutant no longer associates with the α6β4 integrin, but does with the α3β1 integrin. Thus, Sdc1 is required to act with α6β4 integrin in haptotaxis and Sdc4 is required to act via a distinct mechanism with α3β1.

FIGS. 7A-B. Sdc1-specific binding site in β4 integrin cytoplasmic domain. (FIG. 7A) Syndecans. The entire cytoplasmic domains of Sdc1 (SEQ ID NO: 20) and Sdc4 (SEQ ID NO: 21) are shown (Rapraeger & Ott, 1998). C1 and C2 regions are conserved across the syndecan family, whereas the V region is syndecan specific. (FIG. 7B) β4 integrin. The last 30 amino acids of the β4 cytoplasmic domain (over 1,000 amino acids long) are shown (SEQ ID NO: 22), focusing on the last 24 amino acids necessary to bind Sdc1 and Sdc4, as the $β4^{\Delta1729-1752}$ fails to bind either syndecan. Mutation of E1729 to alanine (E1729A) specifically disrupts binding to Sdc4 and the R1733A mutant fails to bind Sdc1.

FIGS. 10A-C. Schematic summary of experiments using either recombinant GST fusion proteins or synthetic peptides to disrupt Sdc1-dependent coupling of HER2 to α6β4 integrin necessary for LPA-induced haptotactic migration. GST-fusion proteins or synthetic peptides were added at concentrations ranging from 0.1 to 30 μM to the culture medium of human HaCat keratinocytes or MCF10A mammary epithelial cells in the presence or absence of 3 μM LPA. The ability of the constructs to inhibit the migration of the cells to close a scratch wound in confluent monolayers was determined and expressed as the concentration of inhibitor necessary to cause 50% inhibition of cell migration. (FIG. 10A) Competition using recombinant GST-fusion proteins. GST-Sdc1 fusion proteins bearing truncations or mutations were assessed for their competitive activity. Proteins that retained the sequence from amino acids 210-240 were found to be fully active, tentatively identifying this as the active site. (FIG. 10B) Competition with synthetic peptides. Peptides were purchased from commercial sources for testing as a putative synstatin inhibitory peptide (SST-$N_{HER2}$). Truncation of the peptide from either end causes loss of activity, indicating that peptide 210-240 is the fully active sequence. (FIG. 10C) Schematic representation of the active site in Sdc1. The active site is shown as a juxtamembrane site in the ectodomain of Sdc1. TM is the transmembrane domain and CYTO is the cytoplasmic domain. The sequence of a peptide derived from this site ($SSTN_{HER2}$) is shown along with its homology across other mammalian Sdc1 species. The human $STTN_{HER2}$ sequence is SEQ ID NO: 23; the homology for $STTN_{HER2}$ across mammals is SEQ ID NO: 24.

FIGS. 11A-F. SSTN treatment of normal (nontransformed) epithelial cells versus carcinoma (transformed) cells. Cells are plated for one day, then treated with either 3-30 μM $SSTN_{IGF1R}$ (SSTN-I), 3-30 μM $SSTN_{EGFR}$ (SSTN-E), 3-30 μM $SSTN_{HER2}$ (SSTN-H) or combinations of the three peptides, each at 10 μM to test their additive effect. Total cell number (a combination of cell proliferation and cell death) is measured using the CellTiterGLO assay (Promega) and is plotted as a percentage of untreated cells after either 4 or 7 days of treatment (less than 0% demonstrates cell death). The treatment times are chosen to reflect only modest effects of the peptides used singly, so that the more pronounced effect of peptides used in combination can still be observed. Treatment for longer times leads to significant cell death observed even with single peptides alone. (FIG. 11A) HaCat human keratinocytes, an example of a normal stratified epithelium, (FIG. 11B) UM-SCC47 cells, a squamous cell carcinoma derived from the tongue of a male patient (a stratified epithelium), (FIG. 11C) SCC25 cells, another squamous cell carcinoma from the tongue of a male patient, (FIG. 11D) MCF10A cells, a normal human breast epithelium, (FIG. 11E) MDA-MB-468 cells, a triple-negative (TN) breast carcinoma, and (FIG. 11F) SKBr3 cells, a HER2+ human breast carcinoma. Note that the "triple-negative" designation of the MDA-MB-468 carcinoma means the cells are negative for progesterone receptor, estrogen receptor and the HER2 kinase. Thus, they would not be expected to rely on HER2. Indeed, these cells are not affected by $SSTN_{HER2}$, either alone or when combined with the other peptides. This shows a high degree of specificity for $SSTN_{HER2}$. Nonetheless, the other three carcinomas are inhibited by $SSTN_{HER2}$, and this is enhanced when $SSTN_{HER2}$ is combined with the other SSTN peptides, leading to obvious cell death (e.g., the number of cells at the end of the experiment are less than at the beginning).

DESCRIPTION OF ILLUSTRATIVE EMBODIMENTS

Figure 1:
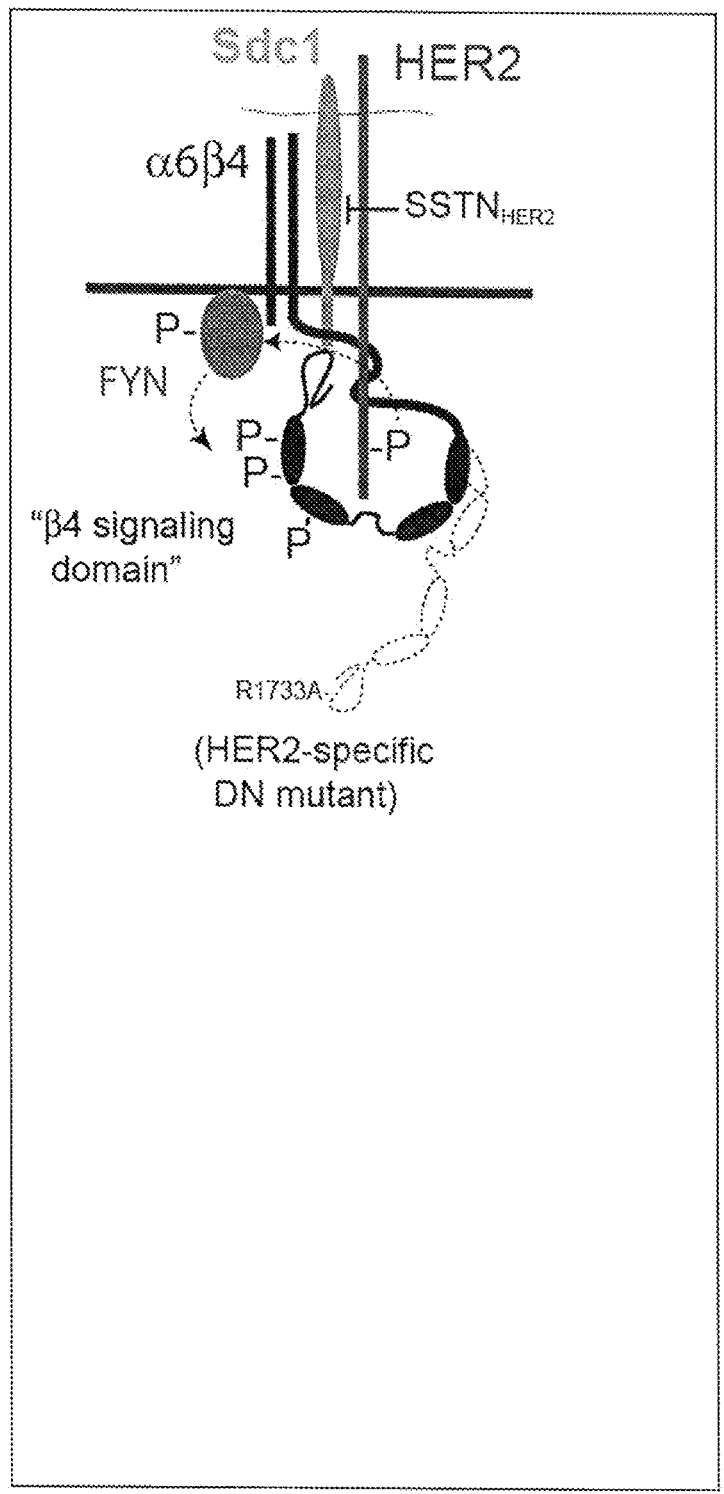
FIG. 1. Putative model of syndecan-coupling of $\alpha6\beta4$ integrin and HER2 in carcinoma. These findings show that Sdc1 couples HER2 to the $\alpha6\beta4$ integrin. This integrin, together with the $\alpha3\beta1$ integrin, is a receptor for LN332 in epithelial cells and endothelial cells. When activated by this kinase, the $\alpha6\beta4$ integrin participates in matrix adhesion and signaling necessary for cell migration, but is also critical for cell survival in tumors. HER2 "activates" the $\alpha6\beta4$ integrin via its activation of Fyn (Wang et al., 2010); Mariotti et al., 2001; Guo et al., 2006), which phosphorylates several tyrosines in the "$\beta4$ signaling domain." Sdc1 binding the $\beta4$ integrin cytoplasmic domain is critical for this signaling cascade, ostensibly by bringing the "signaling domain" to the membrane where it can be phosphorylated by Fyn (Mariotti et al., 2001). Mutation of R1733 (R1733A) in the $\beta4$ integrin cytoplasmic domain disrupts Sdc1 binding. This mutant acts as a dominant negative mutant to specifically disrupt the function of the Sdc1-coupled mechanism during cell migration and tumor cell survival. An extracellular interaction with Sdc1 is also critical for the assembly and function of this complex—potentially acting to capture HER2 with the integrin. Recombinant fragments of the Sdc1 ectodomain block the function of the Sdc1-coupled HER2 complex. This blocking activity is a putative new synstatin ($SSTN_{HER2}$) that the inventor proposes inhibits tumor growth and tumor-induced angiogenesis.

As discussed above, receptor tyrosine kinases play a major role in oncogenesis, particularly in conjunction with integrins. A significant question that has remained unanswered is how the receptor tyrosine kinase associates with the integrin to initiate this process. The inventor now finds that syndecans appear to be the answer (see model of Sdc1 in FIG. 1). He finds that all four members of the syndecan family engage the cytoplasmic domain of the β4 integrin. The focus here will be on Sdc1, which is expressed on epithelial cells (Bernfield et al., 1992; David et al., 1992) and co-immunoprecipitates with the α6β4 integrin and HER2 from activated keratinocytes, A431 cervical carcinoma cells, breast carcinoma cells and HN squamous carcinoma cells (preliminary data and Wang et al., 2010). Importantly, HER2 docks only with Sdc1/α6β4 and not with the other syndecans. The interaction site capturing HER2 appears to be in the Sdc1 extracellular domain, which is distinct from that of other syndecans, and the inventor finds that recombinant Sdc1 peptides mimicking this interaction site (which the inventor calls synstatin-HER2 or $SSTN_{HER2}$) block this interaction. In addition to this extracellular site, he finds that the syndecans also engage distinct sites in the β4 cytoplasmic domain. Sdc1 binding its site in the β4 tail is essential for signaling by this complex, as mutation of this Sdc1-specific site generates a β4 dominant negative mutant (DNM) that specifically blocks the Sdc1-coupled signaling mechanism.

Hints from the inventor's prior work (Wang et al., 2010) already indicated specificity of Sdc1 for α6β4/HER2. The inventor found that A431 carcinoma cells, or HaCat human keratinocytes, relied on the α6β4 integrin for a signaling response that leads to spreading of the cells when plated on LN332, the native ligand for this integrin, or on antibody directed against α6β4 integrin that mimics ligand anchorage. This cell spreading response is completely dependent on Sdc1 and HER2, despite the ability of other syndecans and receptor tyrosine kinases to assemble with the integrin. In a similar fashion, the inventor showed that the survival of the A431 carcinoma cells depends on Sdc1 and the α6β4 integrin, as cell death was caused by disrupting the expression of Sdc1 and disruption of the ability of Sdc1 to engage the cytoplasmic domain of the integrin. However, the details of how Sdc1 exerts this specificity have remained unknown until now.

A number of labs have investigated the potential role of syndecans in α6β4-mediated cell migration and tumorigenesis, but these studies have focused largely on syndecans acting as co-receptors with the α6β4 integrin in laminin binding rather than a role in directly regulating its activation. The phosphorylated and "activated" α6β4 integrin redistributes to the leading edges of invading keratinocytes or tumors; these leading edges overexpress the "unprocessed" form of LN332 that retains the LG4,5 heparin-binding region that engages syndecans (Amano et al., 2000; Marinkovich et al., 1992; Matsui et al., 1995; Goldfinger et al., 1999; Goldfinger et al., 1998). Interestingly, recent work from Rouselle's group shows that Sdc1 and Sdc4 bind differently to the LG4,5 domain and speculates that this may account for somewhat different cell behaviors mediated by these two syndecans (Carulli et al., J2012). Other work shows that expression of LG4,5 supports tumorigenesis in an animal model of squamous cell carcinoma, again suggesting a potential role for syndecans in tumorigenesis (Tran et al., 2008), although it is admittedly indirect. Nonetheless, the inventor has now discovered that assembly of α6β4 integrin and HER2 is regulated by the syndecan family of matrix receptors. In particular, syndecan-1 (Sdc1) links the α6β4 integrin to HER2—a linkage that is required for tumor cell survival. Importantly, the linkage relies on a highly specific motif in the extracellular domain of Sdc1. These and other aspects of the invention are described in detail below.

I. Syndecans

A. The Syndecan Family

Cell surface adhesion receptors physically bind cells to their extracellular matrix (ECM) and couple such interactions to intracellular signaling mechanisms which influence gene expression, cell morphology, motility, growth, differentiation and survival (Roskelley et al., 1995; Miranti and Brugge, 2002). Many ECM ligands contain closely spaced proteoglycan- and integrin-binding domains, indicating that the molecular mechanisms by which cells recognize and interact with their extracellular milieu may involve the formation of signaling complexes containing both proteoglycans and integrins. Consequentially, these two types of receptors may act in concert to modulate cell adhesion and migration. While the role of integrins in cell adhesion and signaling is well established, the role of heparan sulfate proteoglycans (HSPGs) is not well characterized.

The vertebrate syndecans are a family of four transmembrane HSPGs. Endowed by their heparan sulfate (HS) chains, syndecans bind a variety of ECM ligands, including fibronectin (FN), laminin (LN), tenascin, thrombospondin (TSP), vitronectin (VN) and the fibrillar collagens (COL) (Bernfield et al., 1999). While the syndecan HS chains are essential for matrix binding, less is known about the role of syndecan core proteins in cell adhesion signaling, although the core protein can affect ligand binding interactions, as well as occupancy induced signaling (Rapraeger and Ott, 1998; Rapraeger, 2000).

The syndecans display a high degree of conservation within their core proteins both across species and across family members. Like the integrins, the syndecans lack intrinsic signaling activity. Their short cytoplasmic tails (ca. 30 aa) consist of three regions, two of which are conserved amongst the four syndecans (C1 and C2) and which flank an intervening variable (V) region. Proteins known to interact with these conserved domains are believed to link syndecan ligand binding interactions to the transduction of intracellular signals (Couchman et al., 2001). Each family member is uniquely defined by its ectodomains and the V-regions of its cytoplasmic tail. Divergence within these regions is believed to confer separate and distinct functions to each individual family member. Distinct roles for the V-regions of Sdc-2 and -4 in matrix assembly and focal adhesion formation respectively have been described (Klass et al., 2000; Woods and Couchman, 2001); however, specific functions for the syndecan ectodomains are almost wholly unknown with the noted exception of Sdc-1 and -4 which contain binding sites for as yet unidentified cell surface receptor(s) (McFall and Rapraeger, 1997; McFall and Rapraeger, 1998).

B. Syndecan Function in Cell Adhesion and Spreading

Current evidence suggests that the syndecan core proteins participate in adhesion-mediated signaling in collaboration with co-receptors at the cell surface. One example is Sdc-4 in focal adhesion and stress fiber formation, which requires both Sdc-4 and integrin engagement whereas neither is sufficient alone (Woods et al., 1986; Izzard et al., 1986; Streeter and Rees, 1987; Singer et al., 1987). The requirement for Sdc-4 ligation can be overcome by treatment with phorbol esters (Woods and Couchman, 1994) or lysophosphatidic acid (LPA) (Saoncella et al., 1999) implicating PKC and RhoA in Sdc-4 signaling. While the mechanism by which Sdc-4 contributes to RhoA activation is not clear, it is known that Sdc-4 interacts directly with PKC$\alpha$ as well as phosphatidyl inositol 4,5 bisphosphate (PIP2) via its cytoplasmic tail and these interactions potentiate PKC$\alpha$ activity (Oh et al., 1997a; Oh et al., 1997b; Oh et al., 1998; Baciu and Goetinck, 1995).

While the mechanism by which Sdc-1 signals is not clear, there is ample evidence implicating a signaling role for this receptor as well. Ectopic expression of Sdc-1 in Schwann cells enhances cell spreading and promotes the formation of focal adhesions (Hansen et al., 1994) and actin stress fibers (Carey et al., 1994a); similar morphological changes occur when Sdc-1 is co-clustered with antibodies (Carey et al., 1994b). This response requires the cytoplasmic domain, since clustering of a truncated core protein did not induce reorganization of the cytoskeleton. Expression of Sdc-1 in human ARH-77 leukemia cells or hepatocellular carcinoma cells inhibits invasion of cells into COL matrices (Liu et al., 1998; Ohtake et al., 1999). ARH-77 cells expressing a chimera comprised of the Sdc-1 ectodomain fused to the glycosyl-phosphatidyl inositol (GPI) tail of glypican-1 also fail to invade a COL matrix demonstrating that Sdc-1's anti-invasive activity resides in its extracellular domain. In similar studies, Raji human lymphoblastoid cells transfected with mouse Sdc-1 (Raji-S1) spread on TSP, FN and antibodies directed against the Sdc-1 ectodomain (Lebakken and Rapraeger, 1996). This spreading is unaffected by truncation of the cytoplasmic domain, indicating that the Sdc-1 core protein interacts with and cooperatively signals through an associated transmembrane signaling partner. Analogous features have also been observed for Sdc-2 (Granes et al., 1999) and Sdc-4 (Yamashita et al., 1999).

Potential syndecan signaling partners include cell surface integrins. Iba et al. (2000) demonstrated that mesenchymal cells when seeded on an HS-specific ligand, the cysteine rich domain of a disintegrin and metalloprotease, ADAM-12/Meltrin $\alpha$ (rADAM12-cys), will spread in a manner that requires cooperate signaling of both syndecans and $\beta_1$ integrins. These results imply that syndecan(s) can trigger signaling cascades required for cell spreading either by exposing a cryptic binding site for $\beta_1$ integrins, as has been proposed for FN (Khan et al., 1988), or by modulating the activation state of $\beta_1$ integrins. Interestingly, colon carcinoma cells attach but fail to spread on aADAM12-cys. However, exogenous stimulation of $\beta_1$ integrins with $Mn^{2+}$ or $\beta_1$ integrin function activating antibody, mAb 12G10, induced cell spreading, suggesting a mechanism whereby the syndecan activates $\beta_1$ integrins is blocked in transformed cells.

C. Syndecan-1

Syndecan-1 is highly expressed at the basolateral surface of epithelial cells where it is thought to interact with the actin cytoskeleton and to modulate cell adhesion and growth factor signaling (Bernfield et al., 1999; Rapraeger et al., 1986; Kim et al., 1994; Sanderson and Bernfield, 1988). In experimental studies of malignant transformation, Sdc-1 expression is associated with the maintenance of epithelial morphology, anchorage-dependent growth and inhibition of invasiveness. Alterations in syndecan expression during development (Sun et al., 1998) and in transformed epithelial (Inki and Jalkanen, 1996; Bayer-Garner et al., 2001) are associated with an epithelial-mesenchymal transformation with attendant alterations in cell morphology, motility, growth and differentiation. Transfection of epithelial cells with anti-sense mRNA for Sdc-1 or downregulation of Sdc-1 expression by androgen-induced transformation results in an epithelial to mesenchymal transformation and increased invasion (Leppa et al., 1992; Kato et al., 1995; Leppa et al., 1991). The loss of E-cadherin under these circumstances has long suggested a coordinate regulation of Sdc-1 and E-cadherin expression (Sun et al., 1998; Leppa et al., 1996). These studies, as well as others, indicate that there appears to be a threshold requirement for syndecan expression to elicit its biological activity. Syndecan-1 is downregulated in a number of epithelial cancers and in pre-malignant lesions of the oral mucosa (Soukka et al., 2000) and uterine cervix (Inki et al., 1994; Rintala et al., 1999; Nakanishi et al., 1999), and its loss may be an early genetic event contributing to tumor progression (Sanderson, 2001; Numa et al., 2002; Hirabayashi et al., 1998). Loss of Sdc-1 correlates with a reduced survival in squamous cell carcinoma of the head, neck and lung (Anttonen et al., 1999; Inki et al., 1994; Nakaerts et al., 1997), laryngeal cancer (Pulkkinen et al., 1997; Klatka, 2002), malignant mesothelioma (Kumar-Singh et al., 1998) and multiple myeloma (Sanderson and Borset, 2002) and a high metastatic potential in hepatocellular and colorectal carcinomas (Matsumoto et al., 1997; Fujiya et al., 2001; Levy et al., 1997; Levy et al., 1996). Downregulation of Sdc-2 and -4 expression has also been observed in certain human carcinomas (Nakaerts et al., 1997; Park et al., 2002; Mundhenke et al., 2002; Crescimanno et al., 1999), but the functional consequences of these alterations in expression are less clear.

In contrast to the general notion that the syndecan may be an inhibitor of carcinogenesis, Sdc-1 also demonstrates tumor promoter function. Syndecan-1 supplements Wnt-1 induced tumorigenesis of the mouse mammary gland (Alexander et al., 2000) and promotes the formation of metastases in mouse lung squamous carcinoma cells (Hirabayashi et al., 1998). Enhanced Sdc-1 expression has also been observed in pancreatic (Conejo et al., 2000), gastric (Wiksten et al., 2001) and breast (Burbach et al., 2003; Stanley et al., 1999; Barbareschi et al., 2003) carcinomas and this overexpression correlates with increased tumor aggressiveness and poor clinical prognosis. This duality in the role of Sdc-1 in tumorigenesis may reflect tissue and/or tumor stage-specific function, or reflect the multiple functions of this PG.

Sanderson was the first to demonstrate a role for Sdc-1 in tumor cell migration by examining the invasion of myeloma cells into collagen gels (Liu et al., 1998). Ectopic expression of Sdc-1 in syndecan-deficient myeloma cells had the striking effect of curtailing invasion, whereas the expression of other cell surface heparan sulfate PGs (e.g., glypican) was without effect. Using chimeras derived from these two proteins, Sanderson showed that the activity of the syndecan is preserved when its ectodomain alone is expressed as a glycosyl-phosphatidylinositol (GPI)-linked protein at the cell surface. Although clearly responsible for binding the collagen matrix via its attached heparan sulfate chains, the anti-invasive activity of the syndecan requires yet an additional interaction that traces to a site in the extracellular domain of the core protein itself. The mechanism by which the ectodomain site influences the invasion of the myeloma cells is unknown, but its interaction with other cell surface receptors in a "co-receptor" role is one possibility. More recently, ectopic expression of Sdc-1 has also been shown to curtail the invasion of hepatocellular carcinoma cells into a collagen matrix (Ohtake et al., 1999).

II. Integrins and HER2

A. α6β4 Integrin

Integrins are receptors that mediate attachment between a cell and the tissues surrounding it, which may be other cells or the ECM. They also play a role in cell signaling and thereby regulate cellular shape, motility, and the cell cycle.

Typically, receptors inform a cell of the molecules in its environment and the cell responds. Not only do integrins perform this outside-in signalling, but they also operate an inside-out mode. Thus, they transduce information from the ECM to the cell as well as reveal the status of the cell to the outside, allowing rapid and flexible responses to changes in the environment, for example to allow blood coagulation by platelets.

There are many types of integrin, and many cells have multiple types on their surface. Integrins are of vital importance to all animals and have been found in all animals investigated, from sponges to mammals. Integrins have been extensively studied in humans.

Integrins work alongside other proteins such as cadherins, immunoglobulin superfamily cell adhesion molecules, selectins and syndecans to mediate cell-cell and cell-matrix interaction and communication. Integrins bind cell surface and ECM components such as fibronectin, vitronectin, collagen, and laminin.

B. HER2

HER2 (Human Epidermal Growth Factor Receptor 2) also known as Neu, ErbB-2, CD340 (cluster of differentiation 340) or p185 is a protein that in humans is encoded by the ERBB2 gene. HER2 is a member of the epidermal growth factor receptor (EGFR/ErbB) family. Amplification or over-expression of this gene has been shown to play an important role in the pathogenesis and progression of certain aggressive types of breast cancer and in recent years it has evolved to become an important biomarker and target of therapy for the disease.

The ErbB family is composed of four plasma membrane-bound receptor tyrosine kinases. All four contain an extracellular ligand binding domain, a transmembrane domain, and an intracellular domain that can interact with a multitude of signaling molecules. Unlike the other family members, HER2 is considered to be an orphan receptor as it has no known ligand. However, all of the other three ErbB receptors have known ligands and will form either homodimers or heterodimers upon ligand binding. HER2 can heterodimerise with any of the other three receptors and is considered to be the preferred dimerisation partner of the other ErbB receptors. Dimerisation results in the autophosphorylation of tyrosine residues within the cytoplasmic domain of the receptors and initiates a variety of signaling pathways.

Signaling pathways activated by HER2 include:
mitogen-activated protein kinase (MAPK)
phosphoinositide 3-kinase (PI3K/Akt)
phospholipase C γ
protein kinase C (PKC)
signal transducer and activator of transcription (STAT)

HER2 has previously been shown to interact with Beta-catenin, Glycoprotein 130, PLCG1, Erbin, MUC1, Grb2, Heat shock protein 90 kDa alpha (cytosolic), member A1, DLG4, PIK3R2, PICK1 and SHC1. In summary, signaling through the ErbB family of receptors promotes cell proliferation and opposes apoptosis, and therefore must be tightly regulated to prevent uncontrolled cell growth from occurring.

Amplification or over-expression of the ERBB2 gene occurs in approximately 30% of breast cancers. It is strongly associated with increased disease recurrence and a worse prognosis. Over-expression is also known to occur in ovarian, stomach, and aggressive forms of uterine cancer, such as uterine serous endometrial carcinoma. HER2 is co-localized, and, most of the time, co-amplified with the gene GRB7, which is a proto-oncogene associated with breast, testicular germ cell, gastric, and esophageal tumours. HER2 proteins have been shown to form clusters in cell membranes that may play a role in tumorigenesis.

HER2 is the target of the monoclonal antibody trastuzumab (marketed as Herceptin). Trastuzumab is effective only in cancers where HER2 is over-expressed. An important downstream effect of trastuzumab binding to HER2 is an increase in p27, a protein that halts cell proliferation. Another monoclonal antibody, Pertuzumab, which inhibits dimerization of HER2 and HER3 receptors, is in advanced clinical trials.

Additionally, NeuVax (Galena Biopharma) is a peptide-based immunotherapy that directs "killer" T cells to target and destroy cancer cells that express HER2. It has entered phase 3 clinical trials.

It is revealed that patients with ER+ (Estrogen receptor positive)/HER2+ compared with ER−/HER2+ breast cancers may actually benefit more from drugs that inhibit the PI3K/AKT molecular pathway.

Overexpression of HER2 can also be suppressed by the amplification of other genes. Research is currently being conducted to discover which genes may have this desired effect. The expression of HER2 is regulated by signaling through estrogen receptors. Normally, estradiol and tamoxifen acting through the estrogen receptor down-regulate the expression of HER2. However, when the ratio of the coactivator AIB-3 exceeds that of the corepressor PAX2, the expression of HER2 is upregulated in the presence of tamoxifen, leading to tamoxifen-resistant breast cancer. Recent evidence has implicated HER2 signaling in resistance to the EGFR-targeted cancer drug cetuximab.

HER2 testing is performed in breast cancer patients to assess prognosis and to determine suitability for Herceptin therapy. It is important that Herceptin is restricted to HER2-positive individuals as it is expensive and has been associated with cardiac toxicity. For HER2-negative tumors, the risks of Herceptin clearly outweigh the benefits. Tests are usually performed on biopsy samples obtained either by fine-needle aspiration, core needle biopsy, vacuum-assisted breast biopsy, or surgical excision. Immunohistochemistry is used to measure the amount of HER2 protein present in the sample. Alternatively, fluorescence in situ hybridization (FISH) can be used to measure the number of copies of the gene which are present.

The extracellular domain of HER2 can be shed from the surface of tumour cells and enter the circulation. Measurement of serum HER2 by enzyme-linked immunosorbent assay (ELISA) offers a far less invasive method of determining HER2 status than a biopsy and consequently has been extensively investigated. Results so far have suggested that changes in serum HER2 concentrations may be useful in predicting response to Herceptin therapy. However, its ability to determine eligibility for Herceptin therapy is less clear.

III. Syndecan Peptides

A. Structure

The present invention contemplates the design, production and use of various syndecan peptides. The structural features of these peptides are as follows. First, the peptides have about 25 consecutive residues of a syndecan and up to 100 consecutive residues. Thus, the term "a peptide having no more than X consecutive residues," even when including the term "comprising," cannot be understood to comprise a greater number of consecutive syndecan residues. Second, the peptides will contain the motifs responsible for interaction with HER2. In general, the peptides will have, at a minimum, 4 consecutive residues of the syndecan.

In general, the peptides will be 100 residues or less, again, comprising no more than 25-80 consecutive residues of a syndecan. The overall length may be 25, 26, 27, 28, 29, 30, 31, 32, 33, 34, 35, 36, 37, 38, 39, 40, 41, 42, 43, 44, 45, 46, 47, 48, 49, 50, 60, 70, or 80 residues. Ranges of peptide length of 25-50 residues, 31-50 residues, 40-50 residues, 45-50 residues, 25-61, residues, 31-61 residues, 31-80 residues, 25-100 residues, 31-100 residues, and 31-75 residues are contemplated. The number of consecutive syndecan residues may be 25-50 residues, 31-50 residues, 40-50 residues, 45-50 residues, 25-61, residues, 31-61 residues, 31-80 residues, 25-100 residues, 31-100 residues, and 31-75.

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse syndecan peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., 2000.

D. Design, Variants and Analogs

Having identified structures in HER2 interaction with α6β4 integrins, the inventor also contemplates that variants of the sequences may be employed. For example, certain non-natural amino acids that satisfy the structural constraints of the sequences may be substituted without a loss, and perhaps with an improvement in, biological function. In addition, the present inventor also contemplates that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, "molecular modeling" means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., PCT/US99/11913, incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

X-ray Crystallography.

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573, PCT/US99/18441, PCT/US99/11913, and PCT/US00/03745. The disclosures of all these patent documents are incorporated herein by reference in their entirety.

NMR Spectroscopy.

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the interaction of $\alpha 6\beta 4$ and HER2. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

IV. Therapies

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous media. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Cancer Types and Subjects

Cancer cells to which the methods of the present invention can be applied include generally any cell that expresses α6β4 integrin, and more particularly, that overexpresses α6β4 integrin. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

C. Treatment Methods

Peptides or analogs that inhibit α6β4 integrin engagement of HER2 are generally useful as anti-cancer therapeutics or prophylactics. They can be administered to mammalian subjects (e.g., human breast cancer patients) alone or in conjunction with other drugs and/or radiotherapy. The compounds can also be administered to subjects that are genetically and/or environmentally (due to, for example, physiological and/or environmental factors) susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke).

When the methods are applied to subjects with cancer, prior to administration of a compound, the cancer can optionally be tested for α6β4 integrin and HER2 expression or overexpression by methods known in the art. In this way, subjects can be identified as being susceptible to treatments according to the present invention. Such methods can be performed in vitro on cancer cells obtained from a subject. Alternatively, in vivo imaging techniques using, for example, radiolabeled antibodies specific for α6β4 integrin and HER2 can be performed.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 5-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

D. Scarring and other Pathologic Wound Healing

Wound healing is an essential process in maintaining health. However, in certain instances, wound healing can create health problems. These include hypertrophic scarring, keloid or dermoid formation, and exuberant granulation. These conditions are often supported by pathologic angiogenesis (discussed below). The present invention may be applied to address these conditions.

1. Keloids

A keloid is a type of scar which, depending on its maturity, is composed mainly of either type III (early) or type I (late) collagen. It is a result of an overgrowth of granulation tissue (collagen type 3) at the site of a healed skin injury which is then slowly replaced by collagen type 1. Keloids are firm, rubbery lesions or shiny, fibrous nodules, and can vary from pink to flesh-coloured or red to dark brown in colour. A keloid scar is benign, non-contagious, but sometimes accompanied by severe itchiness and pain, and changes in texture. In severe cases, it can affect movement of skin.

Keloids should not be confused with hypertrophic scars, which are raised scars that do not grow beyond the boundaries of the original wound. Keloids expand in claw-like growths over normal skin. They have the capability to hurt with a needle-like pain or to itch without warning, although the degree of sensation varies from patient to patient.

If the keloid becomes infected, it may ulcerate. Removing the scar is one treatment option; however, it may result in more severe consequences: the probability that the resulting surgery scar will also become a keloid is high, usually greater than 50%. Laser treatment has also been used with varying degrees of success.

Keloids form within scar tissue. Collagen, used in wound repair, tends to overgrow in this area, sometimes producing a lump many times larger than that of the original scar. Although they usually occur at the site of an injury, keloids can also arise spontaneously. They can occur at the site of a piercing and even from something as simple as a pimple or scratch. They can occur as a result of severe acne or chickenpox scarring, infection at a wound site, repeated trauma to an area, excessive skin tension during wound closure or a foreign body in a wound. Keloids can sometimes be sensitive to chlorine. Keloid scars can grow, if they appear at a younger age, because the body is still growing.

Histologically, keloids are fibrotic tumors characterized by a collection of atypical fibroblasts with excessive deposition of extracellular matrix components, especially collagen, fibronectin, elastin, and proteoglycans. Generally, keloids contain relatively acellular centers and thick, abundant collagen bundles that form nodules in the deep dermal portion of the lesion. Keloids present a therapeutic challenge that must be addressed, as these lesions can cause significant pain, pruritus (itching), and physical disfigurement. They may not improve in appearance over time and can limit mobility if located over a joint.

Keloids affect both sexes equally, although the incidence in young female patients has been reported to be higher than in young males, probably reflecting the greater frequency of earlobe piercing among women. There is a fifteen times higher frequency of occurrence in highly pigmented people. Persons of African descent are at increased risk of keloid occurrences.

The best treatment is prevention in patients with a known predisposition. This includes preventing unnecessary trauma or surgery (including ear piercing, elective mole removal), whenever possible. Any skin problems in predisposed individuals (e.g., acne, infections) should be treated as early as possible to minimize areas of inflammation.

Intra-Lesional Corticosteroids.

Intra-lesional corticosteroids are first-line therapy for most keloids. A systematic review found that up to 70 percent of patients respond to intra-lesional corticosteroid injection with flattening of keloids, although the recurrence rate is high in some studies (up to 50 percent at five years). While corticosteroids are one of the more common treatments, injections into and in close proximity to keloid tissue can be highly painful and can produce undesirable results in female patients, as per any other testosterone-based treatment.

Excision.

Scalpel excision may be indicated if injection therapy alone is unsuccessful or unlikely to result in significant improvement. Excision should be combined with preoperative, intraoperative, or postoperative triamcinolone or interferon injections. Recurrence rates from 45 to 100 percent have been reported in patients treated with excision alone; this falls to below 50 percent in patients treated with combination therapy.

Gel Sheeting.

Both hydrogel and silicone gel sheeting have been used for the treatment of symptoms (e.g., pain and itching) in patients with established keloids as well as for the management of evolving keloids and the prevention of keloids at the sites of new injuries. While the precise mechanism of action is still poorly understood, there is evidence that application of gel sheeting may reduce the incidence of abnormal scarring. A controlled study found significant changes in growth factor levels of fibronectin and IL-8 with application of hydrogel sheeting with respect to normal skin. Silicone sheeting was associated with changing growth factor levels of only fibronectin.

Cryosurgery.

Most useful in combination with other treatments for keloids. The major side effect is permanent hypopigmentation, which limits its use in people with darker skin.

Radiation Therapy.

Most studies, but not all, have found radiation therapy to be highly effective in reducing keloid recurrence, with improvement rates of 70 to 90 percent when administered after surgical excision. A small randomized trial of treatments after surgery found recurrences in two of sixteen earlobe keloids (13 percent) treated with radiation therapy and in four of twelve earlobe keloids (33 percent) treated with steroid injections. However, concern regarding the potential long-term risks (e.g., malignancy) associated with using radiation for an essentially benign disorder limits its utility in most patients. Only a few cases of malignancy that may have been associated with radiation therapy for keloids have been reported. Although causation cannot be confirmed in these cases, caution should still be used when prescribing radiation therapy for keloids, particularly when treating younger patients. Radiation therapy may occasionally be appropriate as treatment for keloids that are resistant to other therapies. In addition, radiation therapy may be indicated for lesions that are not amenable to resection.

Interferon Alpha.

Interferon alpha injections may reduce recurrence rates postoperatively. However, all currently available studies of interferon therapy suffer from methodologic problems, making an evidence-based recommendation regarding its use difficult.

Pulsed Dye Laser.

Pulsed dye laser treatment can be beneficial for keloids, and appears to induce keloid regression through suppression of keloid fibroblast proliferation, and induction of apoptosis and enzyme activity. Combination treatment with pulsed dye laser plus intralesional therapy with corticosteroids and/or fluorouracil may be superior to either approach alone.

2. Hypertrophic Scarring

Hypertrophic scars are a cutaneous condition characterized by deposits of excessive amounts of collagen which gives rise to a raised scar, but not to the degree observed with keloids. Like keloids, they form most often at the sites of pimples, body piercings, cuts and burns. They often contain nerves and blood vessels. They generally develop after thermal or traumatic injury that involves the deep layers of the dermis and express high levels of TGF-$\beta$.

When a normal wound heals the body produces new collagen fibers at a rate which balances the breakdown of old collagen. Hypertrophic scars are red and thick and may be itchy or painful. They do not extend beyond the boundary of the original wound but may continue to thicken for up to 6 months. They usually improve over the one or two years but may cause distress due to their appearance or the intensity of the itching, also restricting movement if they are located close to a joint.

Hypertrophic scars are more common in the young and people with darker skin. Some people have an inherited tendency to this type of scarring. It is not possible to completely prevent hypertrophic scars, so anyone who has suffered one should inform their doctor or surgeon if they need to have surgery. Scar Therapies are available which may speed up the process of change from a hypertrophic scar to a flatter, paler one. Scars do not occur in younger people as often as older people because their skin cells replicate more quickly and fill in the wound with normal skin tissue.

3. Proud Flesh

Granulation tissue is the perfused, fibrous connective tissue that replaces a fibrin clot in healing wounds. Granulation tissue typically grows from the base of a wound and is able to fill wounds of almost any size it heals. In addition, it is also found in ulcers like esophageal ulcer. However, when the granulation becomes uncontrolled, often resulting from improper wound care, a condition known as exuberant granulation or "proud flesh" results. The scar tissue, if untreated, may completely overtake the wound area. Caught early, the condition can be treated by topical or injected steroids, but more advanced cases require surgical intervention. Horses are subject to this disease, particularly in the legs. Also, some individuals of African decent have a genetic predisposition to exuberant scarring.

E. Pathologic Angiogenesis

Despite the abundancy of angiogenic factors present in different tissues, endothelial cell turnover in a healthy adult organism is remarkably low with a turnover in the order of thousands of days. The maintenance of endothelial quiescence is thought to be due to the presence of endogenous negative regulators. Moreover, positive and negative regulators often co-exist in tissues with extensive angiogenesis. These observations have led to the hypothesis that activation of the endothelium depends on a balance between these opposing regulators. If positive angiogenic factors dominate, the endothelium will be activated. Thus, the angiogenic process can be divided in an activation phase (initiation and progression of the angiogenic process) and a phase of resolution (termination and stabilization of the vessels). It is not yet clear whether the resolution phase is due to upregulation of endogenous inhibitors or exhaustion of positive regulators.

With respect to activated endothelium, an important distinction must be made between physiological and pathological settings. Although many positive and negative regulators operate in both, endothelial cell proliferation is tightly controlled in the former, whereas in the latter, the uncontrolled growth of microvessels may lead to several "angiogenic diseases" in different tissues, such as hemangiomas, psoriasis, Kaposi's sarcoma, ocular neovascularization, rheumatoid arthritis, endometriosis, atherosclerosis, tumor growth and metastasis, myocardial ischemia, peripheral ischemia, cerebral ischemia, wound healing, reconstructive surgery, and ulcer healing, and these may also be advantageously treated with the compositions of the present invention. Some of these are discussed in greater detail below.

Hemangiomas are angiogenic diseases, characterized by the proliferation of capillary endothelium with accumulation of mast cells, fibroblasts and macrophages. They represent the most frequent tumors of infancy, occurring more frequently in females than males (3:1 ratio). Hemangiomas are characterized by rapid neonatal growth (proliferating phase). By the age of 6 to 10 months, the hemangioma's growth rate becomes proportional to the growth rate of the child, followed by a very slow regression for the next 5 to 8 years (involuting phase). Most hemangiomas occur as single tumors whereas about 20% of the affected infants have multiple tumors, which may appear at any body site. Approximately 5% produce life-, sight-, or limb-threatening complications, with high mortality rates. The pathogenesis of hemangiomas has not yet been elucidated. However, several immunohistochemical studies have provided insight into the histopathology of these lesions. In particular, proliferating hemangiomas express high levels of proliferating cell nuclear antigen (PCNA, a marker for cells in the S phase), type IV collagenase, VEGF and FGF-2. During the involuting phase of hemangiomas, expression of these angiogenic factors decreases. Furthermore, urinary levels of FGF-2 are elevated during the proliferating phase of hemangioma, but become normal during involution or after therapy with IFN-α.

Other proliferative disorders of the skin include psoriasis and Kaposi's sarcoma. Hypervascular psoriatic lesions express high levels of the angiogenic inducer IL-8, whereas the expression of the endogenous inhibitor TSP-1 is decreased. Kaposi's sarcoma (KS) is the most common tumor associated with human immunodeficiency virus (HIV) infection and is in this setting almost always associated with human herpes virus 8 (HHV-8) infection. Typical features of KS are proliferating spindle-shaped cells, considered to be the tumor cells and endothelial cells forming blood vessels. KS is a cytokine-mediated disease, highly responsive to different inflammatory mediators like IL-1β, TNF-α and IFN-γ and angiogenic factors. In particular, FGF-2 was found to synergize with HIV-tat to promote angiogenesis and KS development. Finally, growth of KS, both in vitro and in vivo, could be blocked by an antisense oligonucleotide targeting FGF-2.

Diabetic retinopathy is the leading cause of blindness in the working population, but ocular neovascularization can also occur upon exposure of preterm babies to oxygen. It is assumed that both forms are induced by hypoxia in the retina. Elevated levels of the hypoxia-inducible angiogenic factor VEGF were detected in the aqueous and vitreous of eyes with proliferative retinopathy.

Excessive production of angiogenic factors from infiltrating macrophages, immune cells or inflammatory cells may also trigger the formation of pannus, an extensively vascularized tissue that invades and destroys the cartilage, as seen in rheumatoid arthritis. Moreover, uncontrolled angiogenesis may underlie various female reproductive disorders, such as prolonged menstrual bleeding or infertility, and excessive endothelial cell proliferation has been observed in the endometrium of women with endometriosis.

Angiogenesis also contributes to atherosclerosis, a major cause of death of Western populations. Atherosclerosis is the main cause of heart attack. The walls of the coronary artery are normally free of microvessels except in the atherosclerotic plaques, where there are dense networks of capillaries, known as the vasa vasorum. These fragile microvessels can cause hemorrhages, leading to blood clotting, with a subsequent decreased blood flow to the heart muscle and heart attack. Finally, angiogenesis is thought to be indispensable for solid tumor growth and metastasis.

V. Combination Therapies

Tumor cell resistance to DNA damaging agents represents a major problem in clinical oncology. One goal of current cancer research is to find ways to improve the efficacy of chemo- and radiotherapy. One way is by combining such traditional therapies with gene therapy. In the context of the present invention, it is contemplated that syndecan peptide therapy could be used similarly in conjunction with chemotherapeutic, radiotherapeutic, or immunotherapuetic intervention.

To kill cells, inhibit cell growth, inhibit metastasis, inhibit angiogenesis or otherwise reverse or reduce the malignant phenotype of tumor cells, using the methods and compositions of the present invention, one would generally contact a target cell with a syndecan peptide and at least one other therapy. These therapies would be provided in a combined amount effective to kill or inhibit proliferation of the cell. This process may involve contacting the cells with the agents/therapies at the same time. This may be achieved by contacting the cell with a single composition or pharmacological formulation that includes both agents, or by contacting the cell with two distinct compositions or formulations, at the same time, wherein one composition includes the syndecan peptide and the other includes the agent.

Alternatively, the syndecan treatment may precede or follow the other treatment by intervals ranging from minutes to weeks. In embodiments where the other treatment and the syndecan peptide are applied separately to the cell, one would generally ensure that a significant period of time did not expire between the time of each delivery, such that the therapies would still be able to exert an advantageously combined effect on the cell. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) pass between the respective administrations.

It also is conceivable that more than one administration of either the syndecan peptide or the other therapy will be desired. Various combinations may be employed, where the syndecan peptide is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both therapies are delivered to a cell in a combined amount effective to kill the cell.

Agents or factors suitable for use in a combined therapy include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are comtemplated for use with in combination with peptides of the present invention. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with peptides, as described above.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventor proposes that the local or regional delivery of syndecan peptides to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining syndecan therapies with chemo- and radiotherapies, combinations with immunotherapy, hormone therapy, toxin therapy and surgery are also contemplated. In particular, one may employ targeted therapies such as Avastin, Erbitux, Gleevec, Herceptin and Rituxan.

It also should be pointed out that any of the foregoing therapies may prove useful by themselves in treating cancer.

VI. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Antibodies and Reagents.

Antibodies used were mouse mAb 3E1 and P1B5 (Chemicon, Temecula, Calif.) against β4 and β1 integrin extracellular domains, respectively; rabbit antibody Ab1922 (Millipore, Billerica, Mass.) to the β4 cytoplasmic domain; rabbit BM165 (provided by Dr. Peter Marinkovich, Stanford University, CA) against laminin α3 chain; anti-penta histidine antibody (Qiagen, Valencia, Calif.) and goat anti-biotin antibody (Vector Laboratories, Burlingame, Calif.). Rat mAb (mAb13) to human integrin 1 was kindly provided by Dr. Steven Akiyama (NIEHS, National Institutes of Health). The inventor used mouse mAbs B-A38 (Accurate Chemical and Scientific, Westbury, N.Y.) and 150.9 (University of Alabama Hybridoma Facility) to human Sdc1 and human Sdc4, respectively and rat mAb 281.2 (Homan et al., 1998) or KY 8.2 (Echtermeyer et al., 2001) against mouse Sdc1 or mouse Sdc4, respectively. HER2 was recognized by anti-c-ErbB-2 Ab-15 (clone 3B5) (Fisher). EGFR-specific antibody (sc-03-G) was from Santa Cruz.

Dulbecco's modified Eagles medium (DMEM) and rhodamine-conjugated phalloidin were from Invitrogen (Grand Island, N.Y.); Glutathione-conjugated Sepharose beads were from GE Healthcare Biosciences Corp (Piscataway, N.J.); Human recombinant epidermal growth factor (rhEGF) was from Sigma Aldrich (St. Louis, Mo.); Hepatocyte Growth Factor (HGF) was from PEPROTECH (Rocky Hill, N.J.); ErbB2 inhibitor (AG825) was from Chemicon; EGFR inhibitor (Iressa) was kindly provided by Dr. Deric Wheeler (University of Wisconsin, Wis.). Human Sdc1 siRNA (target sequence GGAGGAATTCTATGCCTGA (SEQ ID NO:16)) and human Sdc4 siRNA (target sequence CAGGAATCT-GATGACTTTGAG (SEQ ID NO:17)) were from Ambion. Sdc1 C-terminal peptides were synthesized by Genscript (Piscataway, N.J.).

Yeast Two Hybrid Analysis.

Yeast two hybrid analysis was conducted as described (Wang et al., 2010).

Plasmid Constructs.

The cDNAs of all syndecans were inserted into the pcDNA3 vector using restriction sites engineered into the 5' ends of the primers used to amplify the Syndecan fragments. Deletion of the C2 domain of mouse Sdc1 and Sdc4 in pcDNA3 vector was made by inserting a stop codon before the EFYA sequence by using the Quikchange Site Directed Mutagenesis Kit (Stratagene, La Jolla, Calif.).

The cDNA of human integrin β4 were inserted into pcDNA vector. The cDNA of integrin β4 fragment encoding amino acids 1677-1752 was inserted into pTRC-His A vector; site mutations and deletions were generated by using the Quikchange Site Directed Mutagenesis Kit.

Cell Culture and Transfection.

Human epidermoid carcinoma A431, normal Human HaCat keratinocytes and SKBr3 mammary carcinoma cells were grown in DMEM, supplemented with 10% calf serum or 10% fetal bovine serum (Hyclone Laboratories, Logan, Utah), 4 mM L-glutamine (Sigma), and 100 units/ml penicillin and 100 g/ml streptomycin (Invitrogen) at 37° C. and 92.5% air, 7.5% $CO_2$. MCF10A mammary epithelial cells were grown in DMEM F12 50/50 plus 15 mM Hepes, L-glutamine, 5% horse serum, 10 μg/ml insulin, 0.5 μg/ml hydrocortisone, and 0.02 μg/ml EGF. Cells were transfected with Syndecan or integrin β4 constructs in pcDNA3 using Lipofectamine PLUS (Invitrogen) and 10 μg of plasmid by following the manufacturer's instructions. Stable populations were selected in 1.0 mg/ml G418 (Invitrogen).

Cell Spreading Assays.

Nitrocellulose-coated 10-well glass slides (Erie Scientific, Portsmouth, N.H.) were prepared as described by Beauvais and. Rapraeger (2010). Wells of slide were coated at 37° C. for 2 h with mAb 3E1 (3 μg/ml), diluted in phosphate-buffered saline (CMF-PBS: 135 mM NaCl, 2.7 mM KCl, 10.2 mM $Na_2HPO_4 7H_2O$, and 1.75 mM $KH_2PO_4$, pH 7.4), and blocked with serum-free Hepes-buffered DMEM (pH 7.4) containing 0.1% heat-denatured bovine serum albumin (plating medium). Cells were lifted with trypsin (0.25% w/v), washed with DMEM, and regenerated in suspension for 1 h at 37° C. in DMEM containing 10% fetal bovine serum. Cells were then plated in wells (50 μl/well) in plating medium at $10^5$ cells/ml. Cells were allowed to adhere and spread for 1 h at 37° C., followed by washing in PBS and fixation overnight in 2% paraformaldehyde at 4° C. The fixed cells were stained with rhodamine-conjugated phalloidin as described by Beauvais. Slides were mounted in Immumount (Thermo shandon), and immunofluorescent images were acquired by using a PlanApo 20 (0.75 numerical aperture) objective and a Photometrics CoolSnap ES camera on a Nikon Eclipse TE2000U microscopy system.

siRNA Treatment and Flow Cytometry.

Oligos of siRNAs specific for human Sdc1 or Sdc4 were used as described previously (Beauvais et al., 2004). To measure cell surface syndecan expression, suspended cells were incubated for 1 h on ice with 1 μg of primary antibody per $3 \times 10^5$ cells and then washed and counterstained with Alexa-488-conjugated secondary antibodies and scanned on a FACSCalibur bench top cytometer. Cell scatter and propidium iodide staining profiles were used to gate live, single-cell events for data analysis (Beauvais et al., 2004; Beauvais et al., 2009).

Fusion Protein Expression and Purification.

6×His-β4CD1677-1752 fusion protein was expressed in E. coli by IPTG induction and purified on Ni-NTA beads following cell lysis in 100 mM $NaH_2PO_4$, 10 mM Tris base and 8 M urea, (8.0). GST-S1CD or GST-S4CD fusion proteins expressed in E. coli by IPTG induced and purified on glutathione-sepharose beads following cell lysis in 150 mM NaCl, 20 mM sodium phosphate (pH 7.4) and 1% Triton X-100.

Wound Healing Assay.

HaCat or MCF10A cells were grown to confluence on 48 well-plates were starved for 6 hr by serum deprivation followed by introduction of a scratch wound in the monolayer using 200 μl pipette tip. Cells were cultured an additional 18 hr in DMEM containing mAb 3E1 (10 μg/ml) and goat anti-mouse IgG (50 μg/ml), EGF (10 ng/ml) or HGF (20 ng/ml) to cause cell migration in the presence or absence of inhibitors. Images were acquired using a PlanApo 20 (0.75 numerical aperture) objective and a Photometrics CoolSnap ES camera on a Nikon Eclipse TE2000U microscopy system and wound closure quantified.

Immunoprecipitation.

Immunoprecipitations were carried out as described previously (Beauvais et al., 2004). Cells were washed once with washing buffer (50 mM Hepes, 50 mM NaCl and 10 mM EDTA, pH 7.4) and lysed for 20 min on ice in 1% Triton X-100 containing a 1:1000 dilution of protease inhibitor mixture set III (Calbiochem) in washing buffer. Cell debris was removed by centrifugation at 20,000 g for 15 min at 4°

C. Lysates or 6×His-tagged β4 cytoplasmic domain (amino acids 1677-1752) were incubated at 4° C. overnight with 100 μl Glutathione Sepharos 4B beads (50% in IP wash buffer), GST-S4CD or GST-S1CD in the presence or absence of different peptides. Samples were resolved by electrophoresis under reduced conditions on a 15% Laemmli gel, transferred to Immobilon P, and probed with primary antibody followed by an alkaline phosphatase-conjugated secondary antibody. Visualization of immune-reactive bands was performed using ECF reagent (GE Healthcare) and scanned on a Typhoon Trio Variable Mode Imager (GE-Healthcare) in blue fluorescence.

Cell Proliferation/Apoptosis Assay.

Cells ($5 \times 10^4$/well in a 24-well plate) were treated with activated TAT-peptide (GRKKRRQRRRPKQEEAYA; (SEQ ID NO:18)), inactivated TAT-peptide (GRKKRRQR-RRPKQEEAAA; (SEQ ID NO:19)) or GST fusion protein (GST, GST-S1ED or GST-S4ED). Cells death was observed by trypan blue staining or Cell Tilter-GLO Cell Viability Assay (Promega).

Example 2

Results

Sdc1 Engages the Cytoplasmic Domain of the β4 Integrin.

Syndecan-1 (Sdc1) is typically expressed on epithelial cells and is the most abundant epithelial syndecan. This is particularly true for keratinocytes, which express as much Sdc1 as any cell that the inventor has examined. For this reason, the inventor turned to keratinocytes when the inventor was looking for new Sdc1 binding partners. He initiated a yeast two-hybrid screen in which the Sdc1 cytoplasmic domain was used as bait to screen a cDNA library constructed from human keratinocyte mRNA. The screen identified a cDNA clone encoding a partial fragment (C-terminus) of the β4 integrin cytoplasmic domain. The β4 integrin assembles only with the α6 integrin subunit, forming the α6β4 integrin expressed by epithelial cells to bind LN332. The cDNA clone that contains the syndecan binding site encodes amino acids 1473-1752 (roughly the distal third of the cytoplasmic domain) (Wang et al., 2010). It is also interesting to note that it is this distal third that is called the "signaling domain" because it is the region involved in signaling during tumorigenesis (Guo et al., 2006) (cf. FIG. 1).

There are four members of the syndecan family (Sdc1-Sdc4). These are unified as a family largely due to conserved regions in their cytoplasmic domains (Bernfield et al., 1992; Rapraeger & Ott, 1998). Thus, the inventor next examined whether this binding was a feature specific for Sdc1, or was shared by other members of the family. The inventor found that each of the four syndecan cytoplasmic domains bind the β4 integrin cytoplasmic domain (Wang et al., 2010). The conservation of this interaction across the syndecan family suggested the involvement of the conserved C1 or C2 regions present in the syndecan cytoplasmic domains. This was tested by expressing Sdc1 cytoplasmic domain truncations in which the C1 region, C2 region, or both conserved regions were deleted. The inventor found that the interaction depends to largely on the C2 region at the Sdc1 C-terminus—a sequence consisting of four amino acids ( . . . EFYA-c)—that is conserved in the cytoplasmic domains of all four syndecans (Wang et al., 2010).

Sdc1 Links HER2 to Activation of α6β4 Integrin.

Based on this finding, the inventor investigated the potential functional link between syndecans and the α6β4 integrin using the A431 human squamous carcinoma cell line (FIGS. 2A-E) (Wang et al., 2010). These cells have been used previously to show that the α6β4 integrin mediates adhesion and survival signaling in response to LN332 (Bachelder et al., 1999a; 1999b; Tang et al., 1999; Hinterman et al., 2005). Indeed, the inventor found that the A431 cells attach and spread in a 2 hr assay on LN332. LN332 is potentially recognized by two integrins on these cells—the α6β4 integrin and the α3β1 integrin. Thus, the inventor used blocking antibodies to determine which integrin(s) were involved. He found that cell attachment is almost completely blocked by an antibody (mAb 3E1) that disrupts ligand binding to the α6β4 integrin (FIGS. 2B, 2E). A blocking antibody to β1 integrins, which would α3β1 integrin, had no effect on cell spreading (FIG. 2E). However, the inventor found that Sdc1 was required. The cell spreading was disrupted by treating the cells with heparinase (FIGS. 2C, 2E) or by using siRNA to Sdc1 (FIGS. 2D, 2E), treatments that block the ability of Sdc1 to bind LN332 or, in the case of the siRNA, to couple to α6β4 integrin. Thus, although binding to LN332 by α6β4 integrin does not appear to require the syndecan, cell spreading signals arising from this binding are syndecan-dependent and this syndecan is Sdc1.

Given this potential role of Sdc1 in α6β4 integrin signaling, a number of studies were conducted to define the mechanism (summarized in the model shown in FIG. 1). The inventor found that the spreading of the cells relies on activation of HER2 (ErbB2) and Fyn kinase, which leads to phosphoryhlation of α6β4 integrin in its "signaling domain" (Wang et al., 2010). He also found that the integrin, HER2 (ErbB2), Fyn and PI3K all immunoprecipitate with hSdc1, and, Sdc1 co-precipitates when each of these proteins is immunoprecipitated. The precipitation is not quantitative, suggesting that just a fraction of these proteins (10-20%) in the cell are assembled together into this signaling complex.

The inventor also found that the Sdc1 lacking its C2 domain (mSdc1ΔC2 mutant) is incapable of immunoprecipitating with α6β4 integrin when expressed in cells, again demonstrating the importance of the cytoplasmic domain interaction. He also found that this mutant Sdc1 does not promote α6β4-dependent cell spreading.

Sdc1 Couples to α6β4 Integrin and HER2 for A431 Cell Survival.

The inventor initially tested this model in a physiological in vitro setting using the A431 cells. This experiment takes advantage of the finding that activation of α6β4 integrin signaling in tumor cells deficient in p53, such as the A431 cells, provides protection from apoptosis by activating Akt (Bachelder et al., 199b; Lipscomb et al. 2005; Mercuiro & Rabinovitz, 2001). Thus, the inventor tested whether silencing the expression of Sdc1 in the A431 cells would cause them to go into apoptosis. Indeed, he found that silencing endogenous Sdc1 expression caused an 8-fold increase in apoptosis (to nearly 50% of the cells) after 55 hr as assessed by fluorescent annexin V staining (FIGS. 3A-B). Protection from apoptosis was rescued by expressing mSdc1 in the siRNA-treated cells, but could not be rescued by expressing the mSdc1ΔC2 mutant (FIG. 3B). This effect is consistent with syndecan's role in α6β4 integrin signaling and suggested that the cells cultured in serum were utilizing Sdc1 to activate signaling by the integrin.

Figure 3C:
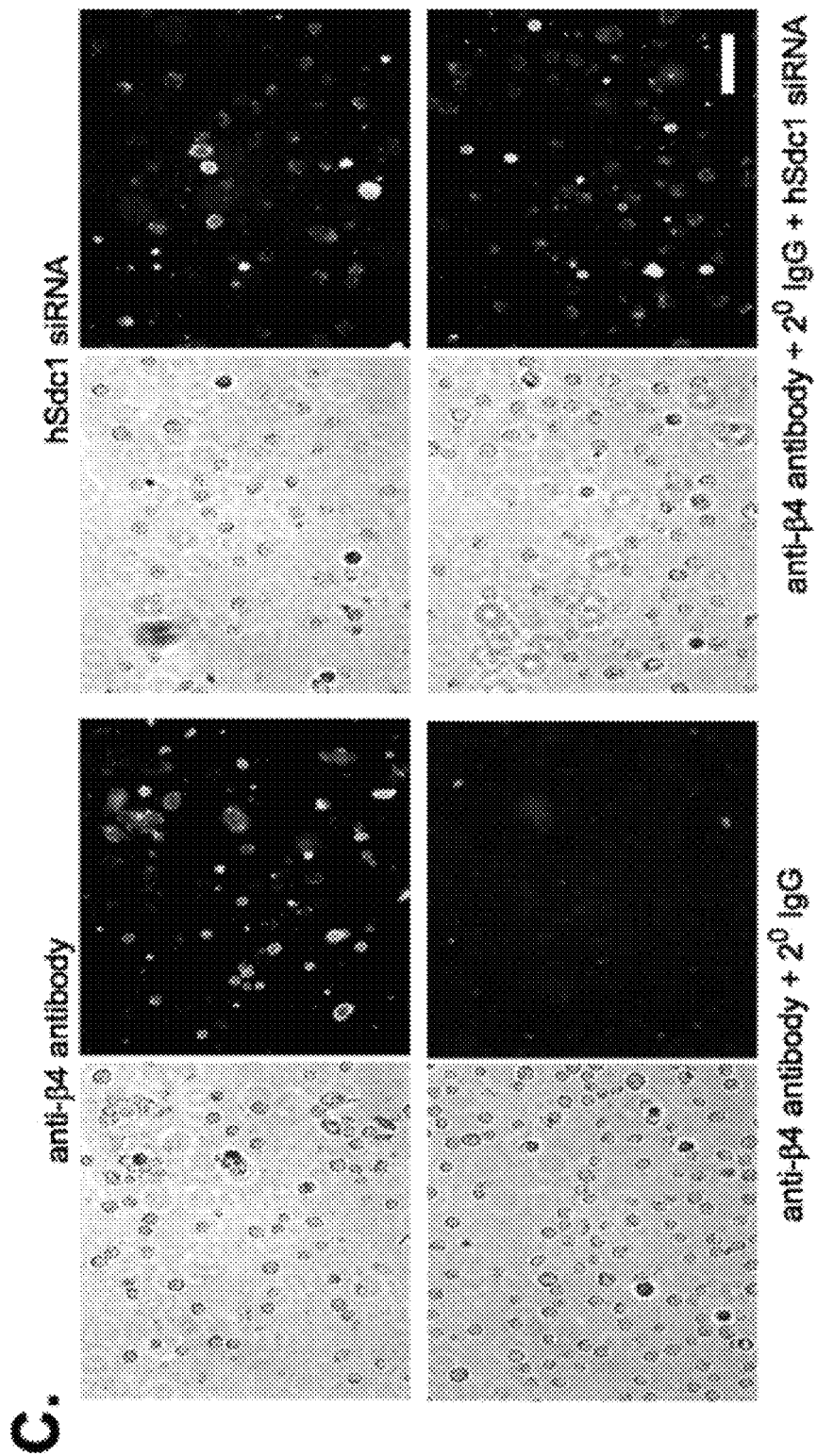
Figure 3D:
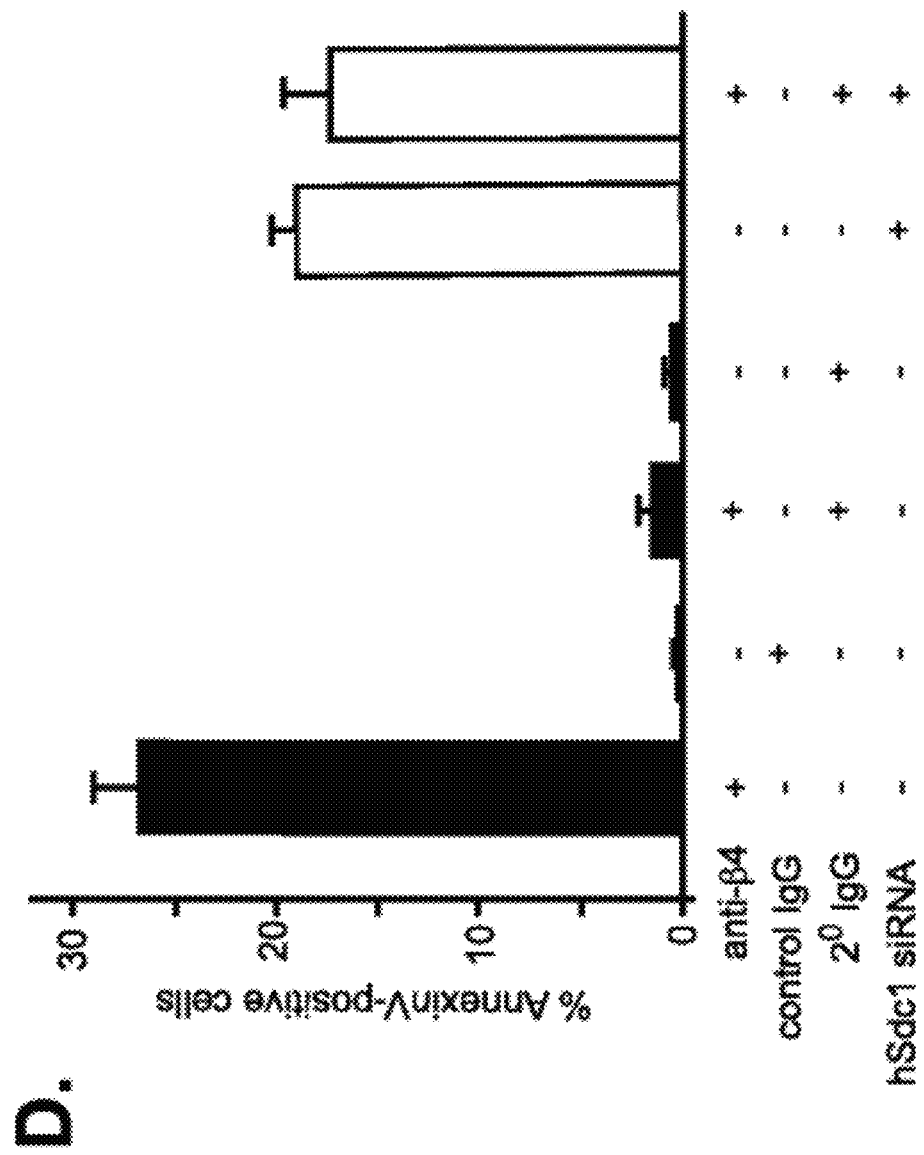

To confirm that the signal was from the α6β4 integrin, A431 cells were cultured for 20 hr in the presence of serum, but also in the presence of the β4-specific antibody 3E1 to block ligand engagement by the integrin. This treatment blocked the anti-apoptotic signal, whereas a control IgG was without effect (FIGS. 3C-D). Secondly, combining the 3E1 treatment with a secondary antibody to cluster the 3E1-integrin complex and thus activate rather than inhibit the integrin reversed the effect of the antibody and provided protection against apoptosis. Lastly, silencing the expression of the endogenous Sdc1 blocked the protective signal provided by the combined 3E1 and clustering antibody treatment (FIG. 3D).

Sdc1, α6β4 Integrin and HER2 Co-Precipitate from Carcinoma Cells.

Figure 4:
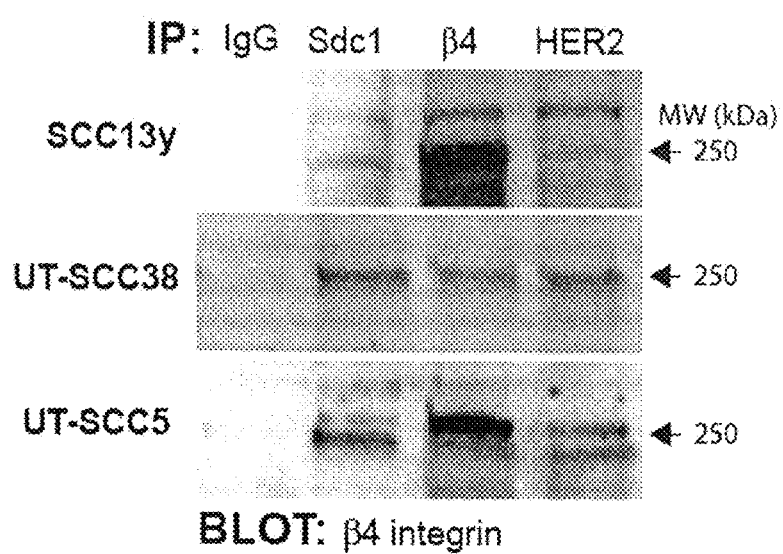
FIG. 4. Co-immunoprecipitation of α6β4 together with Sdc1 and HER2 from HNSCC cells. Sdc4, β4 integrin, and HER2 were immunoprecipitated from lysates of HNSCC cells and probed on Western blots for β4 integrin. Note that the integrin co-precipitates with Sdc1 and with HER2. Note that the integrin subunit is sometimes observed as multiple bands, possibly due to glycosylation differences and proteolytic activity.
Figure 5:
FIG. 5. Sdc1-coupled HER2/α6β4 complex in MCF10 and BT474 mammary cells. Antibodies to Sdc1 or Sdc4 (as a control), β4 integrin, EGFR or HER2 were used to immunoprecipitate the receptors from lysates of MCF10A normal mammary epithelial cells or BT474 (HER2+) carcinoma grown in serum. Blots were then probed for co-precipitation with HER2, which is observed to co-precipitate with Sdc1, the integrin, as well as with EGFR (as a heterodimer).
Figure 8:
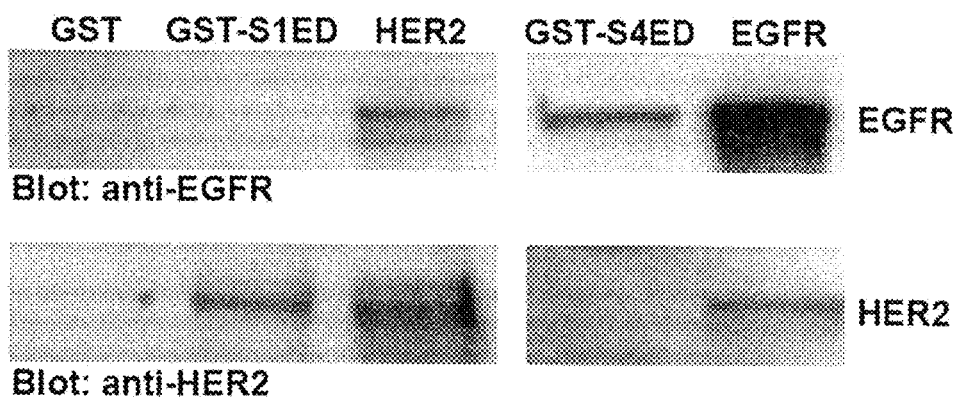
FIG. 8. S1ED and S4ED capture HER2 and EGFR, respectively, from cell lysates. Recombinant Sdc1 and Sdc4 ectodomains (GST-S1ED and GST-S4ED) on glutathione beads are incubated with lysates of EGF-stimulated A431 carcinoma cells, then analyzed for the capture of HER2 or EGFR on western blots. HER2 or EGFR are immunoprecipitated from the lysates directly for comparison. Note that S1ED captures only HER2 and S4ED captures only EGFR.

Taken together, these preliminary studies indicate that Sdc1 is a central mediator of signaling by the β4 integrin subunit that involves its activation by the EGFR family member HER2. Extending this to other cells, the inventor found that α6β4 integrin, Sdc1 and HER2 immunoprecipitate as a receptor complex from several Head and Neck squamous cell carcinomas (SCC) cell lines (FIG. 4) and from MCF10A breast epithelia cells and BT474 human breast carcinoma (FIG. 5). This is specific for Sdc1, as Sdc4 does not co-precipitate with HER2 (FIG. 8). Note that although EGFR and HER2 form heterodimers (shown for the BT474 mammary carcinoma in FIG. 8), Sdc1 does not co-precipitate with EGFR, suggesting that it is not a HER2-EGFR heterodimer that forms a receptor complex with α6β4 integrin and Sdc1, but α6β4 with HER2 alone.

Carcinoma Cell Invasion, Proliferation and Survival Depends on Sdc1-Coupled HER2.

Extending this to further functional studies, it is known that keratinocyte migration depends on the α6β4 and α3β1 integrins to deposit laminin (LN332) and to migrate on this substratum. To demonstrate that engagement of α6β4 integrin with LN332 can stimulate cell migration (haptotaxis), the inventor used a trick of clustering the integrin with antibodies to mimic matrix engagement during a scratch wound assay (FIG. 6A) (Russell et al., 2003; Sehgal et al., 2006). Indeed, the keratinocytes are stimulated to close the wound when treated with lysophosphatidic acid (LPA), which activates Rho G-proteins necessary for cytoskeleton rearrangements, and the α6β4 integrin is clustered with antibodies, mimicking matrix engagement. The inventor terms this "haptotaxis." This haptotaxis is blocked by disrupting activity of the α3β1 integrin or by BM165, an antibody to blocks the integrin binding site in LN332. Next, the inventor tested inhibitors specific for either HER2 or its cousin EGFR—both of which are known to have roles in keratinocyte migration when engaged with the α6β4 integrin Inhibition of HER2 using the tyrphostin AG825 blocks migration, whereas the EGFR specific inhibitor Iressa is without effect. Thus, the migration depends on HER2, much like the cell spreading that the inventor observed earlier that was dependent on HER2 and also on Sdc1. Testing the role of Sdc1 or Sdc4, both of which are expressed by keratinocytes, the inventor found that silencing Sdc1 expression disrupts keratinocyte haptotaxis, and this can be rescued by mouse Sdc1 but not by Sdc1$^{\Delta C2}$ that fails to engage the β4 integrin (FIG. 6B) and which the inventor has shown fails to rescue the integrin activity in cell spreading experiments. A similar experiment conducted with Sdc4 shows that it too blocks migration, but it CAN be rescued by Sdc4$^{\Delta C2}$ that fails to engage the α6β4 integrin (see FIG. 6D). This traces to a role for Sdc4 in associating with and regulating the activity of the α3β1 integrin (FIG. 6D)—which is also required for this migration but via a different syndecan-dependent mechanism.

Figure 9:
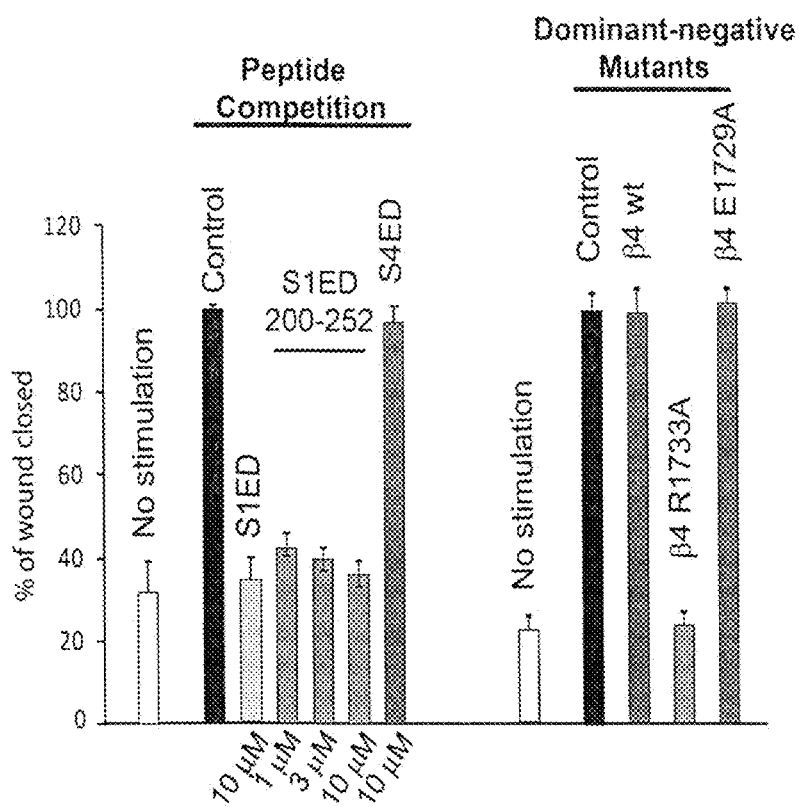
FIG. 9. Sdc1 ectodomain fragments and β4 dominant-negative mutant specific for Sdc1/α6β4/HER2 block MCF10A mammary epithelial cell migration. Haptotaxis of MCF10A human mammary epithelial cells induced by clustering the α6β4 integrin in a scratch wound assay is used to test the efficacy of inhibitors that target the Sdc1 mechanism. Cells are incubated either with entire recombinant syndecan ectodomains (Sdc1 ectodomain (S1ED) or Sdc4 ectodomain (S4ED) as a control), or an active fragment of mouse S1ED ($S1ED^{200-252}$) containing the inhibitory site. Also shown, the $β4^{R1733A}$ integrin mutant, which fails to engage the cytoplasmic domain of Sdc1, also disrupts haptotaxis, whereas the Sdc4-specific dominant negative mutant ($β4^{E1729A}$) is without effect.

The inventor found that the syndecans rely on distinct cytoplasmic and extracellular motifs to assemble these receptor complexes. He found that Sdc1 relies on a QEExYx motfif at its C-terminus to bind the β4 integrin subunit and this binding motif is not found in Sdc4, which relies on a distinct motif. Similarly, the inventor found that the two syndecans engage slightly different sites in the integrin, and that mutation of R1733 in the β4 cytoplasmic domain (β4$^{R1733A}$) reduces its affinity for Sdc1 without affecting its affinity of Sdc4 (summarized in FIGS. 7A-B). When expressed in HaCat keratinocytes or MCF10A mammary epithelial cells, the inventor found that this mutant acts as a dominant negative mutant to block Sdc1-coupled signaling necessary for haptotaxis, supporting the finding that Sdc1 and its coupling to the α6β4 integrin is necessary for this signaling (FIG. 9).

An Interaction Motif in the Sdc1 Ectodomain and Inhibited by SSTN$_{HER2}$, is Required for Carcinoma Cell Invasion and Survival.

The inventor hypothesized that the syndecan ectodomains might also play a role in complex assembly. To test this, the inventor found that beads coated with recombinant Sdc1 ectodomain (GST-S1ED) captures HER2 from A431 carcinoma cell lysates and does not capture EGFR (FIG. 8). In contrast, Sdc4 ectodomain (GST-S4ED) captures EGFR and not HER2. Thus, the specificity of Sdc1 for HER2/α6β4 integrin complex appears to be regulated in part by a recognition site in its extracellular domain.

This finding suggests that the recombinant Sdc1 protein, or peptides derived from it that contain this interaction site, might serve to disrupt the HER2/α6β4 signaling mechanism. Indeed, the inventor found that competition with recombinant S1ED disrupts haptotactic migration of either HaCat keratinocytes (data not shown) or MCF10A mammary epithelial cells (FIG. 9), whereas S4ED is without effect. The reliance of haptotaxis on Sdc1 engagement with the α6β4 integrin is further demonstrated by a blockade of this migration by the β4$^{R1733A}$ DNM that disrupts Sdc1 binding to the integrin, but not by the β4$^{E1729A}$ DNM that blocks Sdc4. The inventor used this assay to further truncate the S1ED recombinant proteins in order to find the smallest peptide that retains full inhibitory activity (e.g., SSTN$_{HER2}$). The inventor tested mouse and human S1ED and find that they compete equally. An example of a test with shortened recombinant fusion proteins is shown in FIG. 9, where mouse S1ED$^{200-252}$ competes for haptotaxis of the MCF10A cells. A summary of these studies is shown in FIGS. 10A-C. The inventor notes that the active motif appears to be within amino acids 210-240 of the human sequence, as any recombinant protein (FIG. 10A) or synthesized peptide (FIG. 10B) that fully contains this sequence retains full competitive activity. Truncation of the sequence from either end (e.g., 210-236 or 214-240) causes loss of activity in the peptides. Note that this putative SSTN (SSTN$_{HER2}$) represents a different site from another synstatin derived from Sdc1 that disrupts an association of Sdc1 with IGF1R (SSTN$_{92-119}$, now called SSTN$_{IGF1R}$) (FIG. 10C). This region contains several highly conserved amino acids, which the inventor is testing to identify those amino acids essential for the inhibitory activity (FIG. 10C).

Signaling from growth factor receptors and integrins is often critical not only for cell migration and tumor cell invasion, but also for cell proliferation and survival. Thus, the inventor has tested the potential role of the Sdc1-coupled α6β4/HER2 mechanism on the growth and survival of either normal epithelial or carcinoma cells using the SSTN$_{HER2}$ peptide. The inventor tested the peptide on the HaCat keratinocytes that he used for migration studies, an example of a normal stratified epithelium, and against the MCF10A cells that the inventor has also used in migration studies, an example of a normal human breast epithelium. The inventor found that although SSTN$_{HER2}$ blocks haptotaxis of these normal cells, it has no effect on their growth or survival when used at concentrations as high as 30 µM (FIGS. 11A-F). He also tested the peptide in combination with other SSTN peptides that the inventor has developed: SSTN$_{IGF1R}$ that targets a Sdc1-αvβ3 integrin-IGF1R receptor complex, and SSTN$_{EGFR}$, that targets a Sdc4-α6β4 integrin-EGFR kinase complex. None of these SSTNs or SSTN combinations affect the normal epithelial cells.

Growth/Survival Mechanisms in the Carcinoma Cells.

In contrast, however, SSTN$_{HER2}$ and the other SSTNs do target the proliferation and survival of carcinoma cells. This includes the UM-SCC47 and SCC25 squamous carcinoma of the human tongue—tumors that are derived from stratified epithelia as are the normal HaCat keratinocytes—and SKBr3 human breast carcinoma cells, representative of tumors arising from breast epithelium that are HER2 positive. Note that the peptide has no effect on the MDA-MB-468 breast carcinoma cells. These are so-called "triple-negative" breast carcinoma cells, and are negative for progesterone receptor, estrogen receptor and HER2. Thus it would be expected that these cells would not be affected by SSTN$_{HER2}$ and they are not, a good indication of the peptide's specificity. These experiments represent relatively short treatment times (4 or 7 days). Nonetheless, cell death is observed in those cases where peptide combinations are used (shown by a reduction in cell number to fewer cells than the number present at the start of the assay). Thus, remarkably, tumor cells but not normal epithelial cells rely on the Sdc1-α6β4-HER2 complex for their growth and survival, and SSTN$_{HER2}$ effectively blocks this dependence, especially when used in combination with other SSTN peptides.

Example 3

Discussion

Epithelial cells rely on the α6β4 integrin to form hemidesmosomes, anchoring the epithelial layer to the ECM and helping it to resist frictional forces. However, during wound healing, or in transformed epithelia overexpressing the HER2, the hemidesmosomes break down in response to HER2 signaling and the free integrin associates with the HER2. HER2 causes phosphorylation of the β4 subunit in its signaling domain, leading to cell proliferation, survival and invasion. The inventor's current work shows that this mechanism relies on association of the integrin with HER2 and Sdc1. Sdc1 engages the cytoplasmic domain of the integrin, ostensibly bringing it to the membrane where it becomes phosphorylated (Wang et al., 2010). But a site in the extracellular domain of Sdc1 is also essential and appears responsible for capturing α6β4 integrin and EGFR as a signaling complex. Competition with either full-length Sdc1 ectodomain expressed as a recombinant protein, or competition with a shorter fragment consisting of amino acids 175-240 or 210-249, (human sequence) identifies the region between 210 and 240 as an inhibitory peptide sequence that serves to block the HER2 stimulated migration of epithelia, and disrupts the proliferation and survival of tumor cells that depend on this mechanism. The inventor proposes that this sequence, which is termed synstatin-HER2 or SSTN$_{HER2}$, is a potential new anti-cancer therapeutic. It acts on breast carcinoma cells, as well as on squamous cell carcinoma—two examples of carcinoma that rely on this signaling mechanism, apparently by competing for the assembly of α6β4 and HER2 with Sdc1. Blockade of this assembly, at a minimum, prevents activation of the α6β4 integrin and may have additional effects on activation of the HER2 as well. Importantly, although blockade of assembly disrupts the migration of normal cells, it does not lead to cell death of normal cells as it does for tumor cells.

This site in Sdc1 is distinct from the well characterized site that couples αvβ3/αvβ5 integrins and IGF1R to Sdc1 (Beauvais & Rapraeger, 2010). This site, amino acids 92-119, is mimicked by SSTN$_{IGF1R}$, which disrupts signaling from the IGF1R-containing complex (Beauvais et al., 2009). SSTN$_{IGF1R}$ does not disrupt the Sdc1-coupled HER2 mechanism, but it does supplement SSTN$_{HER2}$ to cause greater carcinoma cell death when the two synstatins are used together. Importantly, neither peptide causes apoptosis of normal cells.

The α6β4 integrin appears to be expressed with HER2 and EGFR in the vasculature and lymphatics of tumors (Nikolopoulos et al., 2004; Amin et al., 2006; Bruns et al, 2000; Kedar et al., 2002; Bohling et al., 1996; Huang et al., 2002), potentially implicating the Sdc1-coupled mechanisms in angiogenesis. The role of the α6β4 integrin in vascular endothelial cells is not well appreciated, as vascular endothelial cells rapidly lose expression of α6β4 integrin when placed into culture, making it difficult to study (Homan et al., 1998). When expressed artificially in such cells, it is found that they rely on α6β4 integrin to activate Erk and NFκB signaling pathways and migrate to close scratch wounds when plated on LN332 (Nikolopoulos et al., 2004), similar to its role in normal epithelial cells. Work from mouse models of tumorigenesis in vivo are more clear, demonstrating that not only is the integrin expressed in tumor vasculature, but HER2 and EGFR are also expressed, especially in endothelial cells lining blood vessels surrounding tumors (Amin et al., 2006; Bruns et al, 2000; Kedar et al., 2002), and that HER2 and EGFR couple with the α6β4 integrin during tumor-induced angiogenesis (Nikolopoulos et al., 2004). Both Sdc1 and Sdc4 are expressed in the vasculature as well, including tumor vasculature (Beauvais et al., 2009; Echtermeyer et al., 2001; Partovian et al., 2008; Tkachenko et al., 2004). Thus, although the inventor has not yet studied its effects on tumor-induced angiogenesis, it is highly plausible that SSTN$_{HER2}$ targets tumor angiogenesis as well as the growth, survival and invasion of the tumor cells themselves.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. References

The following references, to the extent they provide exemplary procedural or details supplementary to those set forth herein, are incorporated herein by reference:

U.S. Pat. No. 5,440,013
U.S. Pat. No. 5,446,128
U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Pat. No. 7,183,059
U.S. Pat. No. 7,192,713
U.S. Patent Appln. 2005/0015232
Agazie and Hayman, *Mol. Cell. Biol.*, 23(21):7875-7886, 2003.
Alexander et al., *Nat. Genet.*, 25:329-332, 2000.
Amano et al., *J. Biol. Chem.*, 275(30):22728-22735, 2000.
Amin et al., *Cancer Res.*, 66(4):2173-2180, 2006.
Anttonen et al., *Br. J. Cancer*, 79:558-564, 1999.
Bachelder et al., *J. Biol. Chem.*, 274(29):20733-20737, 199a.
Bachelder et al., *J. Biol. Chem.*, 147(5):1063-1072, 1999b.
Baciu and Goetinck, *Mol. Biol. Cell*, 6:1503-1513, 1995.
Barbareschi et al., *Cancer*, 98:474-483, 2003.
Bayer-Garner et al., *J. Cutan. Pathol.*, 28:135-139, 2001.
Beauvais et al., *J. Cell Biol.*, 167(1):171-181, 2004.
Beauvais et al., *J. Exp. Med.*, 206(3):691-705, 2009.
Beauvais and Rapraeger, *J. Cell Sci.*, 123(Pt 21): 3796-807 (2010).
Berger et al., *Cancer Res.*, 48(5):1238-1243, 1988.
Bernfield et al., *Annu. Rev. Biochem.*, 68:729-777, 1999.
Bernfield et al., *Annu. Rev. Cell Biol.*, 8:365-393, 1992.
Bertotti et al., *Cancer Res.*, 65(23):10674-10679, 2005.
Bertotti et al., *J. Cell Biol.*, 175(6):993-1003, 2006.
Bodanszky et al., *J. Antibiot.*, 29(5):549-53, 1976.
Bohling et al., *J Neuropathol Exp Neurol*, 55(5): p. 522-7, 1996.
Bon et al., *Breast Cancer Res*, 9(1):203, 2007.
Boudreau et al., *J. Cell Biol.*, 139(1):257-264, 1997.
Brooks et al., *Cell*, 79:1157-1164, 1994.
Bruns et al., *Cancer Res.*, 60(11):2926-2935, 2000.
Burbach et al., *Matrix Biol.*, 22:163-177, 2003.
Carey et al., *Exp. Cell Res.*, 214:12-21, 1994.
Carey et al., *J. Cell Biol.*, 124:161-170, 1994.
Carey et al., *Otolaryngol. Head Neck Surg.*, 96(3):221-230, 1987.
Carulli et al., *J. Biol. Chem.*, 287(15):12204-12216, 2012.
Cohen et al., *J. Med. Chem.*, 33:883-894, 1990.
Colorado et al., *Cancer Res.*, 60(9):2520-2526, 2000.
Conejo et al., *Int. J. Cancer*, 88:12-20, 2000.
Couchman et al., *Int. Rev. Cytol.*, 207:113-150, 2001.
Crescimanno et al., *J. Pathol.*, 189:600-608, 1999.
Dajee et al., *Nature*, 421(6923):639-643, 2003.
Dans et al., *J. Biol. Chem.*, 276(2):1494-1502, 2001.
Datta et al., *Genes Dev.*, 13(22):2905-2927, 1999.
David et al., *J. Cell Biol.*, 118(4):961-969, 1992.
Dutta and Shaw, *Cancer Res.*, 68(21):8779-8787, 2008.
Echtermeyer et al., *J Clin Invest*, 107(2): p. R9-R14, 2001.
Elenius et al., *J. Cell Biol.*, 114(3):585-595, 1991.
Falcioni et al., *Cancer Res.*, 46(11):5772-5778, 1986.
Falcioni et al., *Exp. Cell Res.*, 236(1):76-85, 1997.
Folgiero et al., *PLoS One*, 3(2):e1592, 2008.
Friedlander et al., *Science*, 270:1500-1502, 1995.
Fujiya et al., *Jpn. J. Cancer Res.*, 92:1074-1081, 2001.
Gallo et al., *J. Invest. Dermatol.*, 107(5):676-683, 1996.
Gambaletta et al., *J. Biol. Chem.*, 275(14):10604-10610, 2000.
Giancotti, *Trends Pharmacol. Sci.*, 28(10):506-511, 2007.
Goldfinger et al., *J. Cell Biol.*, 141(1):255-265, 1998.
Goldfinger et al., *J. Cell Sci.*, 112(Pt 16):2615-2629, 1999.
Gotte et al., *Invest. Ophthal. Visual Sci.*, 43(4):1135-1141, 2002.
Granes et al., *Exp. Cell Res.*, 248:439-456, 1999.
Gronenborn et al., *Anal. Chem.*, 62(1):2-15, 1990.
Guo et al., *Cell*, 126(3):489-502, 2006.
Hansen et al., *J. Cell Biol.*, 126:811-819, 1994.
Hintermann et al., *J. Biol. Chem.*, 280(9):8004-8015, 2005.
Hirabayashi et al., *Tumour Biol.*, 19:454-463, 1998.
Homan et al., *J Cell Sci*, 111 (Pt 18): p. 2717-28, 1998.
Hopkinson and Jones, *Mol. Biol. Cell*, 11(1):277-286, 2000.
Huang et al., *Mol Cancer Ther*, 1(7): p. 507-14, 2002.
Iba et al., *J. Cell Biol.*, 149:1143-1156, 2000.
Inki and Jalkanen, *Ann. Med.*, 28:63-67, 1996.
Izzard et al., *Exp. Cell Res.*, 165:320-336, 1986.
Jackson, *Seminars in Oncology*, 24:L164-172, 1997.
Johnson et al., In: *Biotechnology And Pharmacy*, Pezzuto et al. (Eds.), Chapman and Hall, N.Y., 1993.
Jones et al., *J. Med. Chem.*, 39:904-917, 1996.
Kamphaus et al., *J. Biol. Chem.*, 275(2):1209-1215, 2000.
Kato et al., *Mol. Biol. Cell*, 6:559-576, 1995.
Kedar et al., *Clin. Cancer Res.*, 8(11):3592-3600, 2002.
Khan et al., *J. Biol. Chem.*, 263:11314-113148, 1988.
Kim et al., *Mol. Biol. Cell*, 5:797-805, 1994.
Kimmel and Carey, *Cancer Res.*, 46(7):3614-3623, 1986.
Klass et al., *J. Cell Sci.*, 113:493-506, 2000.
Klatka, *Eur. Arch. Otorhinolaryngol.*, 259:115-118, 2002.
Kumar-Singh et al., *J. Pathol.*, 186:300-305, 1998.
Lebakken, and Rapraeger, *J. Cell Biol.*, 132:1209-1221, 1996.
Leppa et al. *Cell Regul.*, 2:1-11, 1991.
Leppa et al., *J. Cell Sci.*, 109:1393-1403, 1996.
Leppa et al., *Proc. Natl. Acad. Sci. USA*, 89:932-936, 1992.
Levy et al., *Br. J. Cancer*, 74:423-431, 1996.
Levy et al., *Bull. Cancer*, 84:235-237, 1997.
Lipscomb et al., *Cancer Res.*, 65(23):10970-10976, 2005.
Liu et al., *J. Biol. Chem.*, 273:22825-22832, 1998.
Lu et al., *Clin. Cancer Res.*, 14(4):1050-1058, 2008.
Maeshima et al., *J. Biol. Chem.*, 275(28):21340-21348, 2000.
Mainiero et al., *EMBO J.*, 16(9): 2365-2375, 1997.
Mainiero et al., *J. Cell Biol.*, 134(1):241-253, 1996.
Marinkovich et al., *J. Biol. Chem.*, 267(25):17900-17906, 1992.
Mariotti et al., *J. Cell Biol.*, 155(3):447-458, 2001.
Matsui et al., *J. Biol. Chem.*, 270(40):23496-23503, 1995.
Matsumoto et al., *Int. J. Cancer*, 74:482-491, 1997.
McFall and Rapraeger, *J. Biol. Chem.*, 272:12901-12904, 1997.
McFall and Rapraeger, *J. Biol. Chem.*, 273:28270-28276, 1998.

McPherson, *J. Biol. Chem.*, 251:6300-6306, 1976.
Mercurio and Rabinovitz, *Semin. Cancer Biol.*, 11(2):129-141, 2001.
Merdek et al., *J. Biol. Chem.*, 282(41):30322-30330, 2007.
Merrifield, *J. Am. Chem. Soc.*, 85:2149-2154, 1963.
Mertens et al., *J. Biol. Chem.*, 267(28):20435-20443, 1992.
Miranti and Brugge, *Nat. Cell Biol.*, 4:E83-90, 2002.
Mundhenke et al., *Am. J. Pathol.*, 160:185-194, 2002.
Myers et al., *Am. J. Pathology*, 161(6): 2099-2109, 2002.
Myers et al., *J. Cell Biol.*, 148(2): 343-351, 2000.
Nakaerts et al., *Int. J. Cancer*, 74:335-345, 1997.
Nakanishi et al., *Intl. J. Cancer*, 80:527-532, 1999.
Navia et al., *Curr. Opin. Struct. Biol.*, 2:202-210, 1992.
Nievers et al., *Matrix Biol.*, 18(1):5-17, 1999.
Nikolopoulos et al., *Cancer Cell*, 6(5):471-483, 2004.
Numa et al., *Int. J. Oncol.*, 20:39-43, 2002.
Ohtake et al., *Br. J. Cancer*, 81:393-403, 1999.
O'Reilly et al., *Cell*, 79(2):315-328, 1994.
O'Reilly et al., *Cell*, 88(2):277-285, 1997.
Park et al., *J. Biol. Chem.*, 277:29730-29736, 2002.
Partovian et al., *Mol Cell*, 32(1): p. 140-9, 2008.
PCT Appln. PCT/US00/03745
PCT Appln. PCT/US00/14667
PCT Appln. PCT/US99/11913
PCT Appln. PCT/US99/18441
Peptide Synthesis, 1985
Protective Groups in Organic Chemistry, 1973
Protein NMR Spectroscopy, Principles and Practice, J. Cavanagh et al., Academic Press, San Diego, 1996.
Pulkkinen et al., *Acta Otolaryngol.*, 117:312-315, 1997.
Rabinovitz et al., *Mol. Cell Biol.*, 24(10):4351-4360, 2004.
Rapraeger and Ott, *Curr. Opin. Cell Biol.*, 10(5):620-628, 1998.
Rapraeger et al., *J. Cell Biol.*, 103:2683-2696, 1986.
Rapraeger, *J. Cell Biol.*, 149:995-998, 2000.
Remington's Pharmaceutical Sciences, 15th Ed., 1035-1038 and 1570-1580, 1990.
Remington's Pharmaceutical Sciences, 15th Ed., 3:624-652, 1990.
Roskelley et al., *Curr. Opin. Cell Biol.*, 7:736-747, 1995.
Russell et al., *J. Cell Sci.*, 116(Pt 17):3543-3556, 2003.
Sanderson and Bernfield, *Proc. Natl. Acad. Sci. USA*, 85:9562-9566, 1988.
Sanderson and Borset, *Ann. Hematol.*, 81:125-135, 2002.
Sanderson, *Semin. Cell Dev. Biol.*, 12:89-98, 2001.
Santoro et al., *Dev. Cell.*, 5(2):257-271, 2003.
Schafmeister et al., *J. Amer. Chem. Soc.*, 122(24): 5891-5892, 2000.
Sehgal et al., *J. Biol. Chem.*, 281(46):35487-35498, 2006.
Shaw et al., *Cell*, 91(7):949-960, 1997.
Shaw, *Mol. Cell Biol.*, 21(15):5082-5093, 2001.
Singer et al., *J. Cell Biol.*, 104:573-584, 1987.
Slamon et al., *Science*, 235(4785):177-182, 1987.
Solid Phase Peptide Synthelia, 1984
Stanley et al., *Am. J. Clin. Pathol.*, 112:377-383, 1999.
Streeter and Rees, *J. Cell Biol.*, 105:507-515, 1987.
Sun et al., *Int. J. Dev. Biol.*, 42:733-736, 1998.
Tang et al., *Biochem. Biophys. Res. Commun.*, 1264(1):127-132, 1999.
Tkachenko et al., *J Cell Sci*, 117(15): p. 3189-99, 2004.
Tran et al., *Cancer Res.*, 68(8):2885-2894, 2008.
Trusolino et al., *Cell*, 107(5):643-654, 2001.
Tsuruta et al., *Curr. Med. Chem.*, 15(20):1968-1975, 2008.
Van Waes et al., *Cancer Res.*, 51(9):2395-2402, 1991.
Wang et al., *J. Biol. Chem.*, 285:13569-13579, 2010.
Weber, *Advances Protein Chem.*, 41:1-36, 1991.
Wider, *BioTechniques*, 29:1278-1294, 2000.
Wiksten et al., *Int. J. Cancer*, 95:1-6, 2001.
Wilhelmsen et al., *Mol. Biol. Cell*, 18(9):3512-3522, 2007.
Wilhelmsen et al., *Mol. Cell. Biol.*, 26(8):2877-2886, 2006.
Wolf et al., *J. Natl. Cancer Inst.*, 82(19):1566-1572, 1990.
Woods and Couchman, *Curr. Opin. Cell Biol.*, 13:578-583, 2001.
Woods et al., *Embo J.*, 5:665-670, 1986.
Yamashita et al., *J. Immunol.*, 162:5940-5948, 1999.
Yang et al., *Mol. Cell Biol.*, 30(22):5306-5317, 2010.

What is claimed is:

1. A peptide consisting of:
   (a) a peptide segment consisting of between 30 and 100 amino acid residues and comprising residues 210-235 of SEQ ID NO:1, wherein one or more of the between 30 and 100 amino acids are D-amino acids; or
   (b) a peptide segment consisting of between 30 and 100 amino acid residues and comprising residues 210-235 of SEQ ID NO:1, and a blocking agent that is attached to the amino terminal and/or carboxyl terminal residues of the peptide segment.

2. The peptide of claim 1, wherein said peptide segment is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length.

3. The peptide of claim 1, wherein said peptide segment is between 31 and 80 amino acid residues in length.

4. The peptide of claim 1, wherein said peptide segment is between 61 and 80 amino acid residues in length.

5. The peptide of claim 1, wherein said peptide segment is between 66 and 80 amino acid residues in length.

6. The peptide of claim 1, wherein said peptide segment comprises residues 210-240 of SEQ ID NO:1 (SEQ ID NO:3).

7. The peptide of claim 1, wherein said peptide segment consists of residues 210-235 of SEQ ID NO:1 (SEQ ID NO:2) or residues 210-240 of SEQ ID NO:1 (SEQ ID NO:3).

8. The peptide of claim 1, wherein said peptide segment consists essentially of residues 210-240 of SEQ ID NO:1 (SEQ ID NO:3), 210-249 of SEQ ID NO:1 (SEQ ID NO: 4), 175-235 of SEQ ID NO:1 (SEQ ID NO:5) or 175-240 of SEQ ID NO:1 (SEQ ID NO:6).

9. The peptide of claim 1, wherein said peptide segment consists of residues 210-240 of SEQ ID NO:1 (SEQ ID NO: 3), 210-249 of SEQ ID NO:1 (SEQ ID NO: 4), 175-235 of SEQ ID NO:1 (SEQ ID NO: 5) or 175-240 of SEQ ID NO:1 (SEQ ID NO: 6).

10. The peptide of claim 1, wherein said peptide segment is between 31 and 61 amino acid residues in length.

11. A method of inhibiting scarring in a subject comprising administering to said subject the peptide of claim 1, whereby scarring is inhibited in the subject.

12. A method of inhibiting pathologic neovascularization in a subject comprising administering to said subject the peptide of claim 1, whereby pathological neovascularization is inhibited in the subject.

13. The method of claim 12, wherein said peptide segment is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 70, 75, 80, 85, 90, 95 or 100 amino acid residues in length.

14. The method of claim 12, wherein said peptide segment is between 31 and 80 amino acid residues in length.

15. The method of claim 12, wherein said peptide segment is between 61 and 80 amino acid residues in length.

16. The method of claim 12, wherein said peptide segment is between 66 and 80 amino acid residues in length.

17. The method of claim 12, wherein said peptide segment consists essentially of residues 210-235 of SEQ ID NO:1 (SEQ ID NO: 2) or residues 210-240 of SEQ ID NO:1 (SEQ ID NO:3).

18. The method of claim 12, wherein said peptide segment comprises residues 210-240 of SEQ ID NO:1 (SEQ ID NO:3).

19. The method of claim 12, wherein said peptide segment consists essentially of residues 210-240 of SEQ ID NO:1 (SEQ ID NO: 3), 210-249 of SEQ ID NO:1 (SEQ ID NO: 4), 175-235 of SEQ ID NO:1 (SEQ ID NO: 5) or 175-240 of SEQ ID NO:1 (SEQ ID NO: 6).

20. The method of claim 12, wherein said peptide segment consists of residues 210-240 of SEQ ID NO:1 (SEQ ID NO:3), 210-249 of SEQ ID NO:1 (SEQ ID NO:4), 175-235 of SEQ ID NO:1 (SEQ ID NO:5) or 175-240 of SEQ ID NO:1 (SEQ ID NO:6).

21. The method of claim 12, wherein said pathological neovascularization involves activated vascular endothelial cells.

* * * * *

SEQUENCE LISTING

```
<160> NUMBER OF SEQ ID NOS: 24

<210> SEQ ID NO 1
<211> LENGTH: 310
<212> TYPE: PRT
<213> ORGANISM: Homo sapiens

<400> SEQUENCE: 1

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110
```

```
Gly Leu Thr Ala Arg Glu Gln Glu Ala Thr Pro Arg Pro Arg Glu Thr
            115                 120                 125

Thr Gln Leu Pro Thr Thr His Gln Ala Ser Thr Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Ser Ala Thr Glu Arg Ala Ala
            180                 185                 190

Glu Asp Gly Ala Ser Ser Gln Leu Pro Ala Ala Glu Gly Ser Gly Glu
            195                 200                 205

Gln Asp Phe Thr Phe Glu Thr Ser Gly Glu Asn Thr Ala Val Val Ala
            210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
            275                 280                 285

Glu Glu Pro Lys Gln Ala Asn Gly Gly Ala Tyr Gln Lys Pro Thr Lys
            290                 295                 300

Gln Glu Glu Phe Tyr Ala
305                 310

<210> SEQ ID NO 2
<211> LENGTH: 26
<212> TYPE: PRT
<213> ORGANISM: Homo sapiens

<400> SEQUENCE: 2

Asp Phe Thr Phe Glu Thr Ser Gly Glu Asn Thr Ala Val Val Ala Val
1               5                   10                  15

Glu Pro Asp Arg Arg Asn Gln Ser Pro Val
            20                  25

<210> SEQ ID NO 3
<211> LENGTH: 31
<212> TYPE: PRT
<213> ORGANISM: Homo sapiens

<400> SEQUENCE: 3

Asp Phe Thr Phe Glu Thr Ser Gly Glu Asn Thr Ala Val Val Ala Val
1               5                   10                  15

Glu Pro Asp Arg Arg Asn Gln Ser Pro Val Asp Gln Gly Ala Thr
            20                  25                  30

<210> SEQ ID NO 4
<211> LENGTH: 40
<212> TYPE: PRT
<213> ORGANISM: Homo sapiens

<400> SEQUENCE: 4

Asp Phe Thr Phe Glu Thr Ser Gly Glu Asn Thr Ala Val Val Ala Val
1               5                   10                  15

Glu Pro Asp Arg Arg Asn Gln Ser Pro Val Asp Gln Gly Ala Thr Gly
```

```
                20                  25                  30

Ala Ser Gln Gly Leu Leu Asp Arg
        35                  40

<210> SEQ ID NO 5
<211> LENGTH: 61
<212> TYPE: PRT
<213> ORGANISM: Homo sapiens

<400> SEQUENCE: 5

Leu His Thr Pro His Thr Glu Asp Gly Gly Pro Ser Ala Thr Glu Arg
1               5                   10                  15

Ala Ala Glu Asp Gly Ala Ser Ser Gln Leu Pro Ala Ala Glu Gly Ser
                20                  25                  30

Gly Glu Gln Asp Phe Thr Phe Glu Thr Ser Gly Glu Asn Thr Ala Val
            35                  40                  45

Val Ala Val Glu Pro Asp Arg Arg Asn Gln Ser Pro Val
50                  55                  60

<210> SEQ ID NO 6
<211> LENGTH: 66
<212> TYPE: PRT
<213> ORGANISM: Homo sapiens

<400> SEQUENCE: 6

Leu His Thr Pro His Thr Glu Asp Gly Gly Pro Ser Ala Thr Glu Arg
1               5                   10                  15

Ala Ala Glu Asp Gly Ala Ser Ser Gln Leu Pro Ala Ala Glu Gly Ser
                20                  25                  30

Gly Glu Gln Asp Phe Thr Phe Glu Thr Ser Gly Glu Asn Thr Ala Val
            35                  40                  45

Val Ala Val Glu Pro Asp Arg Arg Asn Gln Ser Pro Val Asp Gln Gly
50                  55                  60

Ala Thr
65

<210> SEQ ID NO 7
<211> LENGTH: 31
<212> TYPE: PRT
<213> ORGANISM: Pan troglodytes

<400> SEQUENCE: 7

Asp Phe Thr Phe Glu Thr Ser Gly Glu Asn Thr Ala Val Val Ala Val
1               5                   10                  15

Glu Pro Asp His Arg Asn Gln Ser Pro Val Asp Gln Gly Ala Thr
                20                  25                  30

<210> SEQ ID NO 8
<211> LENGTH: 31
<212> TYPE: PRT
<213> ORGANISM: Macaca mulatta

<400> SEQUENCE: 8

Asp Phe Thr Phe Glu Thr Ser Gly Glu Asn Thr Ala Ile Val Ala Val
1               5                   10                  15

Glu Pro Asp His Arg Asn Gln Ser Pro Val Asp Pro Gly Ala Thr
                20                  25                  30

<210> SEQ ID NO 9
<211> LENGTH: 31
```

<212> TYPE: PRT
<213> ORGANISM: Nomascus

<400> SEQUENCE: 9

Asp Phe Thr Phe Glu Thr Ser Gly Glu Asn Thr Ala Val Ala Val
1               5                   10                  15

Glu Pro Asp His Arg Asn Gln Ser Pro Val Asp Gln Gly Ala Thr
            20                  25                  30

<210> SEQ ID NO 10
<211> LENGTH: 31
<212> TYPE: PRT
<213> ORGANISM: Mus musculus

<400> SEQUENCE: 10

Asp Phe Thr Phe Glu Thr Ser Gly Glu Asn Thr Ala Val Ala Val
1               5                   10                  15

Glu Pro Gly Leu Arg Asn Gln Pro Pro Val Asp Glu Gly Ala Thr
            20                  25                  30

<210> SEQ ID NO 11
<211> LENGTH: 31
<212> TYPE: PRT
<213> ORGANISM: Rattus norvegicus

<400> SEQUENCE: 11

Asp Phe Thr Phe Glu Thr Ser Gly Glu Asn Thr Ala Val Ala Gly Val
1               5                   10                  15

Glu Pro Asp Leu Arg Asn Gln Ser Pro Val Asp Glu Gly Ala Thr
            20                  25                  30

<210> SEQ ID NO 12
<211> LENGTH: 31
<212> TYPE: PRT
<213> ORGANISM: Sus scrofa

<400> SEQUENCE: 12

Asp Phe Thr Phe Asp Val Ser Gly Glu Asn Thr Ala Gly Asp Ala Leu
1               5                   10                  15

Asp Pro Asp Gln Arg Asn Glu Pro Pro Val Asp Gln Gly Thr Thr
            20                  25                  30

<210> SEQ ID NO 13
<211> LENGTH: 31
<212> TYPE: PRT
<213> ORGANISM: Canis familiaris

<400> SEQUENCE: 13

Asp Phe Thr Phe Asp Val Ser Gly Glu Asn Thr Ala Gly Thr Ala Val
1               5                   10                  15

Glu Pro Asp Gln Arg Asn Gln Pro Pro Val Asp Arg Gly Ala Thr
            20                  25                  30

<210> SEQ ID NO 14
<211> LENGTH: 31
<212> TYPE: PRT
<213> ORGANISM: Cricetus cricetus

<400> SEQUENCE: 14

Asp Phe Thr Phe Glu Thr Ser Gly Glu Asn Thr Ala Val Ala Ala Ile
1               5                   10                  15

Glu Pro Asp Gln Arg Asn Gln Pro Pro Val Asp Glu Gly Ala Thr

<210> SEQ ID NO 15
<211> LENGTH: 40
<212> TYPE: PRT
<213> ORGANISM: Gallus gallus

<400> SEQUENCE: 15

Glu Val Ser Glu Asp Gly Ser Gly Asp Pro Gly Asp Phe Ile Leu Val
1               5                   10                  15

Lys Asp Glu Asp Leu Val Pro Thr Gln Asn Ser Glu Val Pro Ala Asp
                20                  25                  30

Ser Gly Arg Asn Ala Lys Ala Ala
            35                  40

<210> SEQ ID NO 16
<211> LENGTH: 19
<212> TYPE: DNA
<213> ORGANISM: Artificial Sequence
<220> FEATURE:
<223> OTHER INFORMATION: Synthetic primer

<400> SEQUENCE: 16
ggaggaattc tatgcctga                                                19

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
caggaatctg atgactttga g                                             21

<210> SEQ ID NO 18
<211> LENGTH: 18
<212> TYPE: PRT
<213> ORGANISM: Artificial Sequence
<220> FEATURE:
<223> OTHER INFORMATION: Synthetic peptide

<400> SEQUENCE: 18

Gly Arg Lys Lys Arg Arg Gln Arg Arg Pro Lys Gln Glu Glu Ala
1               5                   10                  15

Tyr Ala

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Gly Arg Lys Lys Arg Arg Gln Arg Arg Pro Lys Gln Glu Glu Ala
1               5                   10                  15

Ala Ala

<210> SEQ ID NO 20
<211> LENGTH: 34
<212> TYPE: PRT
<213> ORGANISM: Artificial Sequence
<220> FEATURE:

<223> OTHER INFORMATION: Synthetic peptide

<400> SEQUENCE: 20

Arg Met Lys Lys Lys Asp Glu Gly Ser Tyr Ser Leu Glu Glu Pro Lys
1               5                   10                  15

Gln Ala Asn Gly Gly Ala Tyr Gln Lys Pro Thr Lys Gln Glu Glu Phe
            20                  25                  30

Tyr Ala

<210> SEQ ID NO 21
<211> LENGTH: 28
<212> TYPE: PRT
<213> ORGANISM: Artificial Sequence
<220> FEATURE:
<223> OTHER INFORMATION: Synthetic peptide

<400> SEQUENCE: 21

Arg Met Lys Lys Lys Asp Glu Gly Ser Tyr Asp Leu Gly Lys Lys Pro
1               5                   10                  15

Ile Tyr Lys Lys Ala Pro Thr Asn Glu Phe Tyr Ala
            20                  25

<210> SEQ ID NO 22
<211> LENGTH: 30
<212> TYPE: PRT
<213> ORGANISM: Artificial Sequence
<220> FEATURE:
<223> OTHER INFORMATION: Synthetic peptide

<400> SEQUENCE: 22

Thr Arg His Val Thr Gln Glu Phe Val Ser Arg Thr Leu Thr Thr Ser
1               5                   10                  15

Gly Thr Leu Ser Thr His Met Asp Gln Gln Phe Phe Gln Thr
            20                  25                  30

<210> SEQ ID NO 23
<211> LENGTH: 31
<212> TYPE: PRT
<213> ORGANISM: Homo sapiens

<400> SEQUENCE: 23

Asp Phe Thr Phe Glu Thr Ser Gly Glu Asn Thr Ala Val Val Ala Val
1               5                   10                  15

Glu Pro Asp Arg Arg Asn Gln Ser Pro Val Asp Gln Gly Ala Thr
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature

```
<222> LOCATION: (23)..(24)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 24

Asp Phe Thr Phe Glu Xaa Ser Gly Glu Asn Thr Ala Xaa Xaa Ala Val
1               5                   10                  15

Glu Pro Xaa Xaa Arg Asn Xaa Xaa Pro Val Asp Xaa Gly Xaa Thr
            20                  25                  30
```